United States Patent
Stern et al.

[11] Patent Number: 6,130,351
[45] Date of Patent: Oct. 10, 2000

[54] CONTINUOUS PROCESS FOR THE PREPARATION OF N-(PHOSPHONOMETHYL) IMINODIACETIC ACID

[75] Inventors: Michael K. Stern, Clayton; Todd J. Johnson, Columbia; Amy L. Jorgenson, Richmond Heights; Michael D. Rogers; Thaddeus S. Franczyk, II, both of Maryland Heights, all of Mo.

[73] Assignee: Monsanto Company, St. Louis, Mo.

[21] Appl. No.: 09/373,106

[22] Filed: Aug. 12, 1999

Related U.S. Application Data

[60] Provisional application No. 60/096,205, Aug. 12, 1998.

[51] Int. Cl.$^7$ .................................................... C07F 9/38
[52] U.S. Cl. ............................................. 562/17; 562/18
[58] Field of Search ................................ 562/11, 16, 17, 562/18

[56] References Cited

U.S. PATENT DOCUMENTS

| | | | |
|---|---|---|---|
| 2,757,200 | 7/1956 | Jones et al. | 260/604 |
| 2,757,204 | 7/1956 | Ratcliff | 260/604 |

(List continued on next page.)

FOREIGN PATENT DOCUMENTS

| | | |
|---|---|---|
| 0 1445 265 A2 | 6/1985 | European Pat. Off. . |
| 0 170 830 A1 | 2/1986 | European Pat. Off. . |
| 0 197 659 A1 | 10/1986 | European Pat. Off. . |
| 0 207 580 A1 | 1/1987 | European Pat. Off. . |
| 0 216 745 A1 | 4/1987 | European Pat. Off. . |
| 263 624 A2 | 4/1988 | European Pat. Off. . |
| 0 281 707 A2 | 9/1988 | European Pat. Off. . |
| 0 315 716 A1 | 5/1989 | European Pat. Off. . |
| 0 413 068 A1 | 2/1991 | European Pat. Off. . |
| 0 680 948 A1 | 11/1995 | European Pat. Off. . |
| 0 779102 A1 | 6/1997 | European Pat. Off. . |
| 35-4315 | 4/1960 | Japan . |
| 2 252 770 | 8/1992 | United Kingdom . |
| WO 98/35930 | 8/1998 | WIPO . |

OTHER PUBLICATIONS

CA:127:65516 abs of JP09157233, Jun. 1997.

(List continued on next page.)

*Primary Examiner*—Johann Richter
*Assistant Examiner*—Jean F Vollano
*Attorney, Agent, or Firm*—Senniger, Powers, Leavitt & Roedel

[57] ABSTRACT

A process for the production of N-(phosphonomethyl) iminodiacetic acid. N-(acetyl)iminodiacetic acid is formed in a amidocarboxymethylation reactor system, into which a source of each of the following is continuously fed: (1) acetamide or an acetamide derivative, (2) formaldehyde or a formaldehyde generator or derivative, (3) a carbonylation catalyst, (4) carbon monoxide, and optionally (5) hydrogen. In turn, an amidocarboxymethylation reaction product stream, which contains N-(acetyl)iminodiacetic acid and the carbonylation catalyst, is withdrawn from the amidocarboxymethylation reactor system. The carbonylation catalyst is separated from the amidocarboxymethylation reaction product stream to recover the carbonylation catalyst and form a catalyst depleted product stream which contains N-(acetyl)iminodiacetic acid. The separated carbonylation catalyst is returned to the amidocarboxymethylation reactor system, and the N-(acetyl)iminodiacetic acid in the catalyst depleted product stream is either: (1) reacted with a source of phosphorous and a source of formaldehyde in the presence of an acid to form a phosphonomethylation reaction product stream containing N-(phosphonomethyl) iminodiacetic acid and acetic acid; or (2) deacylated and cyclized to form a 2,5-diketopiperazine, and then reacted with a source of phosphorous and a source of formaldehyde in the presence of an acid to form a phosphonomethylation reaction product stream containing N-(phosphonomethyl) iminodiacetic acid and acetic acid. Either way, the N-(phosphonomethyl)iminodiacetic acid is precipitated from the phosphonomethylation reaction product stream in the presence of acetic acid, and the precipitate is recovered to form a filtrate stream.

19 Claims, 2 Drawing Sheets

U.S. PATENT DOCUMENTS

| | | | |
|---|---|---|---|
| 2,757,205 | 7/1956 | Metzweiller et al. | 260/604 |
| 2,757,206 | 7/1956 | Jones et al. | 260/604 |
| 3,246,024 | 4/1966 | Gwynn et al. | 260/439 |
| 3,260,745 | 7/1966 | Andress, Jr. et al. | 260/534 |
| 3,288,846 | 11/1966 | Irani et al. | 260/500 |
| 3,766,266 | 10/1973 | Wakamatsu et al. | 260/534 |
| 3,847,997 | 11/1974 | Allen | 260/604 HF |
| 3,904,668 | 9/1975 | Gaudette et al. | 260/465.5 A |
| 3,969,398 | 7/1976 | Hershman | 260/502.5 |
| 3,998,887 | 12/1976 | Allen | 260/606.5 P |
| 4,225,458 | 9/1980 | Huang et al. | 252/413 |
| 4,264,515 | 4/1981 | Stern et al. | 260/404 |
| 4,312,662 | 1/1982 | Gaertner | 71/86 |
| 4,400,330 | 8/1983 | Wong et al. | 260/502.5 F |
| 4,533,500 | 8/1985 | Chauvin et al. | 554/163 |
| 4,624,937 | 11/1986 | Chou | 502/180 |
| 4,657,705 | 4/1987 | Huang et al. | 562/17 |
| 4,696,772 | 9/1987 | Chou | 260/502.5 F |
| 4,804,499 | 2/1989 | Miller et al. | 562/12 |
| 4,918,222 | 4/1990 | Lin et al. | 562/518 |
| 4,954,466 | 9/1990 | Weisenfeld | 502/24 |
| 5,068,404 | 11/1991 | Miller et al. | 502/17 |
| 5,237,104 | 8/1993 | Summerlin | 568/451 |
| 5,527,953 | 6/1996 | Jones et al. | 562/17 |

OTHER PUBLICATIONS

A. Dorfman et al. "Kinetics and Mechanism of the Oxidative Alkoxylation of Tetraphosphorus in the Presence of Copper (II) Sulfates and Carboxylates" Kinetics and Catalysis, vol. 36, No. 1, pp. 93–100 (1995).

J. Franz et al. "Methods of Preparing Glyphosate" in *Glyphosate: A Unique Global Herbicide*, Chapter 8, pp. 233–262 (American Chemical Society, Washington, D.C., 1997).

J. Parnaud et al. "Some Aspects of the Catalytic Synthesis of N–acyl–α–Aminoacids by Carbonylation of Aldehydes in the Presence of Amides" Journal of Molecular Catalysis, vol. 6, pp. 341–350 (1979).

H. Wakamatsu et al. "Synthesis of N–Acyl Amino–Acids by a Carbonylation Reaction" Chemical Communications, p. 1540 (1971).

R. Weisenfeld "Metal–Catalyzed Carbonylation of Acetamide: Homogeneous–Phase Recovery of Cobalt from a Water–Soluble Amino Acid" Ind. Eng. Chem. Res., vol. 31, No. 2, pp. 636–638 (1992).

F. Bartha et al. "Plant Growth Regulator Precursors Comprising N–(phosphonomethyl)glycine or its Derivative And Carbonates" Chemical Abstract, vol. 113, No. 36393 (1989).

C. Chai et al. "Reactivities of Piperazine–2,5–diones In Radical Bromination Reactions" Chemical Abstract, vol. 126, No. 157470 (1996).

G. Evans et al. "Synthetic And Catalytic Studies of Polymer–Bound Metal Carbonyls" Journal of Organometalic Chemistry, 67, pp. 295–314 (1974).

J. Knap et al. "Dicobalt Octacarbonyl: Kinetics Of The Synthesis At High Pressure" High Pressure Technology, Chemical Engineering Progress Progress Symposium Series, No. 76, vol. 63, pp. 47–54 (19—).

A. J. Moffat "The Use Of Solid Polymeric Ligands In A New Oxo Catalyst recovery And Recycle System" Journal of Catalysis, vol. 19, pp. 322–329 (1970).

D. Riley et al. "Homogeneous Catalysts For Selective Molecular Oxygen Driven Oxidative Decarboxylations" J. Am. Chem. Soc., vol. 113, pp. 3371–3378 (1991).

D. Riley et al. "Vanadium (IV, V) Salts As Homogeneous Catalysts For The Oxygen Oxidation of N–(Phosphonomethyl)Iminodiacetic Acid To N–(Phosphonomethyl)Glycine" Inorg. Chem., vol 30, pp. 4191–4197 (1991).

J. Knifton "Amidocarbonylation" Applied Homogeneous Catalysis with Organometallic Compounds, vol. 1, pp. 159–168 (ed. by Cornils & Herrmann, Weinheim Germany, 1996).

CONTINUOUS PROCESS FOR THE PREPARATION OF N-(PHOSPHONOMETHYL) IMINODIACETIC ACID

CROSS REFERENCE TO RELATED APPLICATION

This patent claims priority from U.S. Provisional Application Ser. No. 60/096,205, filed Aug. 12, 1998.

BACKGROUND OF THE INVENTION

1. Field of the Invention

The present invention relates, in general, to a continuous process for the preparation of N-(phosphonomethyl) iminodiacetic acid wherein the process includes an amidocarboxymethylation step.

2. Description of Related Art

N-(phosphonomethyl)glycine, also known by its common name glyphosate, is a highly effective and commercially important herbicide useful for combating the presence of a wide variety of unwanted vegetation, including agricultural weeds. Between 1988 and 1991, approximately 13 to 20 million acres per year worldwide were treated with glyphosate, making it one of the most important herbicides in the world. Convenient and economical methods of preparing glyphosate and other amino carboxylic acids are, therefore, of great importance.

Franz, et al. in *Glyphosate: A Unique Global Herbicide* (ACS Monograph 189, 1997) at p. 233–257 identify a number of routes by which glyphosate can be prepared. According to one of these, iminodiacetic acid disodium salt (DSIDA) is treated with formaldehyde and phosphorous acid or phosphorous trichloride to produce N-(phosphonomethyl)-iminodiacetic acid and sodium chloride. A carboxymethyl group on the N-(phosphonomethyl) iminodiacetic acid is then oxidatively cleaved in the presence of a carbon catalyst to produce glyphosate acid. A significant drawback of this method is that it produces three equivalents of sodium chloride per equivalent of glyphosate as a side product. Sodium chloride streams of this nature are difficult to recycle because typically after precipitation the salt contains significant quantities of entrapped organic matter. Such entrapped organic matter prevents the sodium chloride from being used for many purposes, for example in foods or feed. Further recrystallization of the sodium chloride adds cost which makes recycle economically unfeasible. Alternate methods of disposing of sodium chloride without detriment to the environment are expensive and difficult.

SUMMARY OF THE INVENTION

This invention provides for a well-defined, low-cost process for the production of N-(phosphonomethyl)-iminodiacetic acid in which sodium chloride is not generated as a by-product.

In the process of the present invention, N-acetyliminodiacetic acid is formed via a continuous amidocarboxymethylation reaction. In this reaction, N-(acetyl) iminodiacetic acid is formed in a amidocarboxymethylation reactor system, into which a source of each of the following is fed continuously: (1) acetamide or an acetamide derivative, (2) formaldehyde or a formaldehyde generator or derivative, (3) a carbonylation catalyst, (4) carbon monoxide, and optionally (5) hydrogen. In turn, an amidocarboxymethylation reaction product stream, which contains N-(acetyl)iminodiacetic acid and the carbonylation catalyst, is withdrawn from the amidocarboxymethylation reactor system. The carbonylation catalyst is separated from the amidocarboxymethylation reaction product stream to recover the carbonylation catalyst and form a catalyst depleted product stream which contains N-(acetyl) iminodiacetic acid. The separated carbonylation catalyst is returned to the amidocarboxymethylation reactor system, and the N-(acetyl)iminodiacetic acid in the catalyst depleted product stream is either: (1) reacted with a source of phosphorous and a source of formaldehyde in the presence of an acid to form a phosphonomethylation reaction product stream containing N-(phosphonomethyl)iminodiacetic acid and acetic acid; or (2) deacylated and cyclized to form a 2,5-diketopiperazine, and then reacted with a source of phosphorous and a source of formaldehyde in the presence of an acid to form a phosphonomethylation reaction product stream containing N-(phosphonomethyl)iminodiacetic acid and acetic acid. Either way, the N-(phosphonomethyl) iminodiacetic acid is precipitated from the phosphonomethylation reaction product stream in the presence of acetic acid, and the precipitate is recovered to form a filtrate stream. The filtrate stream is separated into an acetic acid enriched stream and an acetic acid depleted stream. At least a portion of the acetic acid enriched stream is fed to an acetamide synthesis reactor into which ammonia is simultaneously fed to form an acetamide product stream, which is fed (directly or indirectly) back to the amidocarboxymethylation reactor system.

Further scope of the applicability of the present invention will become apparent from the detailed description provided below. It should be understood, however, that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE PREFERRED EMBODIMENTS

Figure 1:
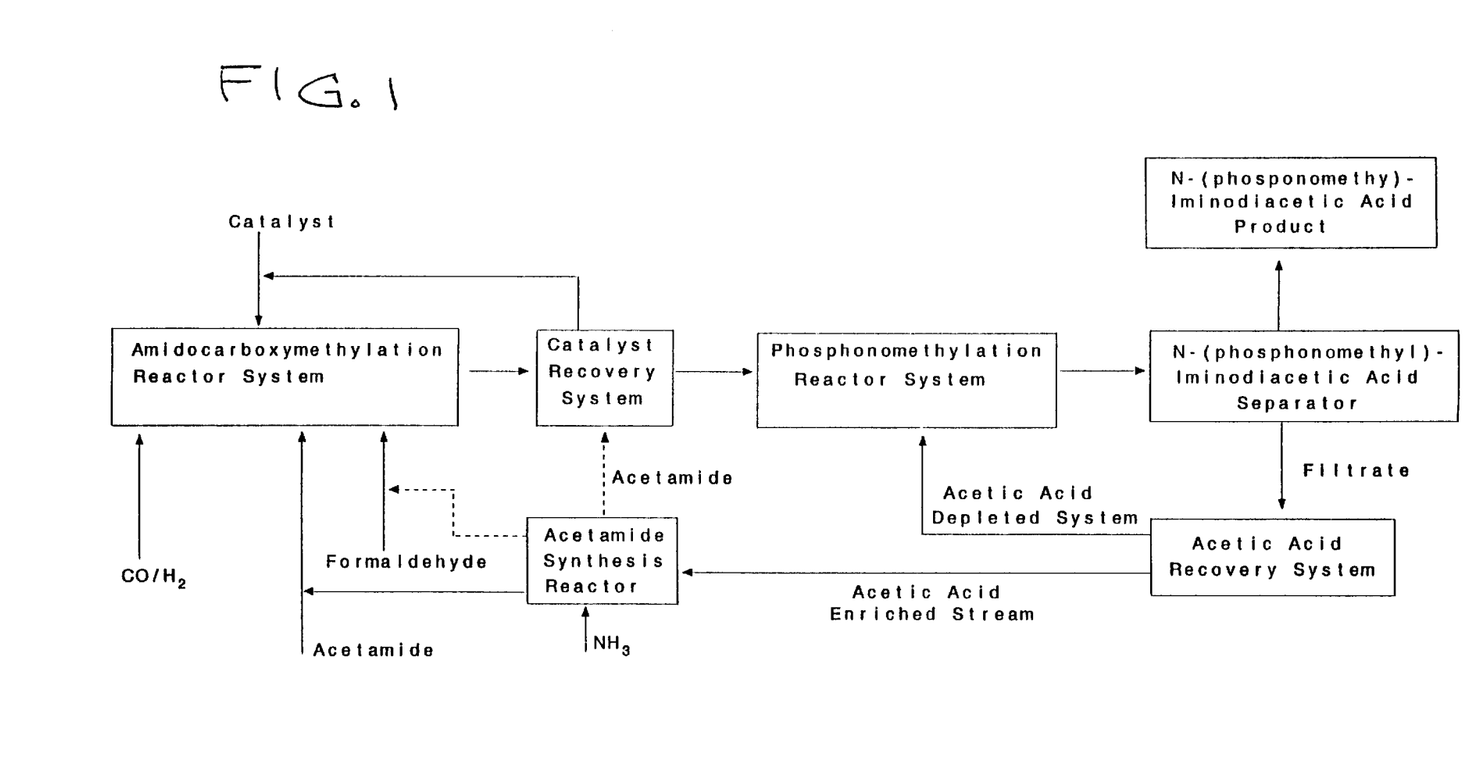
FIG. 1 is a schematic illustration of a preferred embodiment of a process flow diagram for the continuous process of the present invention.

Referring now to FIG. 1, N-acetyliminodiacetic acid is formed in a continuous amidocarboxymethylation reactor system. The feed to the reactor system includes a source of each of (1) acetamide or an acetamide derivative such as diacetamide, triacetamide, hydroxymethyl acetamide or methylene bisacetamide, (2) formaldehyde, a formaldehyde generator such as trioxymethylene or polyoxymethylene, or a formaldehyde derivative such as formacetal or formacylate, (3) a carbonylation catalyst, and (4) carbon monoxide or a carbon monoxide and hydrogen mixture.

An amidocarboxymethylation reaction product stream containing N-acetyliminodiacetic acid product is withdrawn from the reactor system and fed to a catalyst recovery system. The recovered carbonylation catalyst is regenerated, as necessary, and returned to the amidocarboxymethylation reactor system. Solvent is removed from the amidocarboxymethylation reaction product stream and the remainder of the stream is fed to a phosphonomethylation reactor system along with formaldehyde and a source of phosphorous (e.g., $PCl_3$ or $H_3PO_3$) to generate a phosphonomethylation reaction product mixture containing, among other things, N-(phosphonomethyl) iminodiacetic acid and acetic acid. The phosphonomethylation reaction product mixture is then fed to a separator to recover N-(phosphonomethyl)-iminodiacetic acid from the reaction product mixture. A portion of the balance of the reaction product mixture is purged from the system and the remainder is fed to an acetic acid recovery system. Exiting the acetic acid recovery system are two streams. One of these streams is enriched in acetic acid and is fed to the acetamide synthesis reactor. The other is depleted in acetic acid and is returned to the phosphonomethylation reactor system.

In the acetamide synthesis reactor system, acetic acid is reacted with ammonia to generate an acetamide product. The acetamide product them may optionally be mixed with a solvent and returned to the amidocarboxymethylation reactor system or this mixture may be first combined with formaldehyde to generate hydroxymethylacetamide or methylene bisacetamide which is then fed to the amidocarboxymethylation reactor system. As described in greater detail elsewhere herein, a portion of the acetamide may optionally be fed to the catalyst recovery system.

A. Amidocarboxymethylation Reactor System and Reaction

In general, the amidocarboxymethylation reactor system may include one, two or more reaction vessels. For example, the reactor system may comprise several, e.g., three, continuously stirred autoclaves arranged in series. Alternatively, the reactor system may comprise a single stirred autoclave followed by a plug flow reactor or a loop reactor of the type routinely used in oxo-type processes. In general, the first reaction vessel is preferably selected to achieve a relatively high level of conversion of acetamide (or acetamide derivative) to N-(acetyl)iminodiacetic acid, e.g., preferably at least about 65%, more preferably at least about 85%. To achieve such conversions, the first reaction vessel desirably provides excellent gas/liquid mixing. In the second vessel (and subsequent vessels, if employed), conversion to N-(acetyl)iminodiacetic acid is taken to at least about 95% and preferably at least about 98%.

The amidocarboxymethylation reaction is generally carried out at a pressure from about 200 psi to about 4000 psi (about 1,400 kPa to about 28,000 kPa). Preferably, the pressure is at least 500 psi (3,500 kPa), more preferably at least about 1,500 psi (10,500 kPa), and most preferably about 3,000 to about 3,500 psi (21,000–24,000 kPa).

The temperature for the amidocarboxymethylation reaction may be any temperature at which the reactants and equipment can be conveniently handled. Typically, the reaction temperature will be within the range of about 50° C. to about 170° C., preferably is about 65° C. to about 140° C., more preferably is about 80° C. to about 130° C., and still more preferably is about 95° C. to about 115° C.

The amidocarboxymethylation reaction can be run in the presence of a solvent that is chemically and physically compatible with the reaction mixture. In general, the solvent may be an ether, a ketone, an ester, a nitrile, a carboxylic acid, a formamide such as dimethylformamide, or a mixture thereof. Preferably, the solvent is an ether, a ketone, or a nitrile. More preferably, the solvent is an ethylene glycol ether such as dimethoxyethane (DME), an ether such as tetrahydrofuran (THF) or t-butyl methyl ether, acetone, 2-butanone, acetonitrile, or acetic acid.

In a preferred embodiment, the amidocarboxymethylation reaction is carried out in the presence of water. In this embodiment, the molar ratio of water to acetamide (or acetamide derivative) in the amidocarboxymethylation reaction mixture is generally less than about 10:1, preferably between about 1:1 and about 5:1, more preferably between about 1.5:1 and about 5:1, and most preferably between about 1.65:1 and about 4.5:1.

The amidocarboxymethylation reaction can be run in an atmosphere of pure carbon monoxide. Alternatively, diluent gases such as hydrogen, nitrogen, or helium may be introduced along with carbon monoxide into the amidocarboxymethylation reactor. Preferably, the atmosphere contains a significant partial pressure of hydrogen. Typically, the partial pressure ratio of carbon monoxide to hydrogen will be at least about 1:1, preferably about 70:30 to about 99:1, and more preferably from about 85:15 to about 97:3.

Any of a variety of materials constituting a source of a carbonylation catalyst is fed to the amidocarboxymethylation reactor. The catalyst source material may thus be the active form of the catalyst itself. Alternatively, the catalyst source material may be a precursor to or derivative of the catalyst with the active form of the catalyst being generated in the carboxymethylation reactor.

In general, the amidocarboxymethylation catalyst source material contains any composition known to be useful in amidocarboxymethylation reactions and generally contains a metal from Group VIII of the Periodic Table (CAS version). The catalyst source material preferably contains cobalt or palladium, more preferably contains cobalt, and still more preferably is derived from cobalt metal, cobalt oxide, organic and inorganic salts, for example, halides such as cobalt chloride and cobalt bromide, aromatic and aliphatic carboxylates such as cobalt acetate, cobalt propionate, cobalt octanoate, cobalt stearate, cobalt benzoate and cobalt naphthenate, and complex compounds containing one or more ligands such as carbonyls, nitriles and phosphines. The preferred cobalt containing amidocarboxymethylation catalyst source is dicobalt octacarbonyl ($Co_2(CO)_8$), hydridocobalttetracarbonyl ($HCo(CO)_4$), cobalt tetracarbonyl anion ($[Co(CO)_4]^{-1}$) or a cobalt(II) salt.

Experimental evidence obtained to-date suggests that the amidocarboxymethylation reaction is preceded by the formation of a base pair between acetamide (or an acetamide derivative) and the amidocarboxymethylation catalyst source. When the catalyst comprises cobalt, the base pair has the formula $BH^+[Co(CO)_4]^-$ wherein B can be a protonated acetamide or acetamide derivative. In one embodiment of the present invention, therefore, the amidocarboxymethylation catalyst source is reacted with acetamide (or an acetamide derivative) outside the amidocarboxymethylation reactor vessel and the base pair is fed to the reaction vessel. Alternatively, acetamide and the amidocarboxymethylation catalyst source are separately introduced to the reaction vessel and the base pair is formed in situ.

Acetamide may be fed to the amidocarboxymethylation reactor in a variety of forms. For example, it may be fed as a solution containing at least about 3 wt %, preferably at least about 6 wt %, and more preferably between about 10 wt % and about 30 wt % acetamide in any of the above-mentioned solvents, preferably tetrahydrofuran ("THF"), acetone or acetic acid. The acetamide feed may contain other amide derivatives that either hydrolyze or react to give products equivalent to the amidocarboxymethylation of acetamide. These derivatives, for example, could be diacetamide, triacetamide, methylenebis acetamide or hydroxymethylacetamide, bishydroxymethylacetamide or mixtures thereof. The weight percentage of these derivatives in the feed solution could vary from trace components, i.e., less than about 1 wt %, to major components preferably in the range from about 6 wt % to about 30 wt %.

The mole ratio of amidocarboxymethylation catalyst metal atoms to acetamide (or acetamide derivative) fed to the amidocarboxymethylation reactor system can vary over the range of about 0.001 to about 0.3. Preferably, it is about 0.03 to about 0.15, more preferably about 0.06 to about 0.1.

Formaldehyde may be fed to the amidocarboxymethylation reactor vessel in various forms. For example, a 50% formalin solution or a slurry of paraformaldehyde with water and optionally acetic acid may be fed to the reactor vessel. Alternatively, more concentrated formaldehyde solutions may be desirable. For instance, solutions of about 70 wt % formaldehyde, generated either from the dissolution of paraformaldehyde in the appropriate amount of water, or via distillation/concentration of 37–50 wt % formalin, can be used.

In one embodiment, an acid co-catalyst is included in the reaction mixture. The co-catalyst may be a mineral acid such as sulfuric acid, sulfonic acid, phosphorous acid, phosphoric acid, or hydrochloric acid. Preferably, the acid co-catalyst is an organic acid, such as a carboxylic acid, having a $pK_a$ greater than about 3. The organic acid co-catalyst can be, for example, formic acid, acetic acid, or propionic acid, preferably formic acid or acetic acid, and most preferably acetic acid. The molar ratio of acetic acid to cobalt is generally in the range of about 2 to about 60, preferably about 7 to about 55, and still more preferably about 10 to about 50. When acetic acid is employed as a co-catalyst, it has been observed in the case of the continuous amidocarboxymethylation reaction, that the rate of the reaction is increased as compared to reactions carried out in the absence of acetic acid.

When acetic acid is used as a co-catalyst at relatively lower pressures, for example, pressures less than about 1,800 psi (12,500 kPa), the molar ratio of acetic acid to cobalt is generally in the range of about 2 to about 20, preferably about 7 to about 15, and still more preferably about 11 to about 13. At intermediate pressures, for example, pressures within the range of about 1,800 to about 2,500 psi (12,500 to about 17,250 kPa), the molar ratio of acetic acid to cobalt is generally in the range of about 2 to about 45, preferably about 8 to about 30, and still more preferably about 10 to about 20. At relatively high pressures, for example, pressures of at least about 2,500 psi (17,250 kPa), the molar ratio of acetic acid to cobalt is generally in the range of about 3 to about 60, preferably about 8 to about 55, and still more preferably about 10 to about 50.

Payload is measured as the mass (grams, $g_c$) of acetamide divided by the mass (grams, $g_r$) of reaction mixture. One skilled in the art will recognize that useful ranges of payload will depend in part upon the reaction conditions employed and the compatibility of acetamide with the solvents used. The payload typically will vary through the range of about 0.02 grams of acetamide per gram of reaction mixture ($g_c/g_r$) to about 0.3 $g_c/g_r$. Preferably, the payload is about 0.04 to about 0.18 $g_c/g_r$, and more preferably about 0.08 to about 0.13 $g_c/g_r$.

The residence time of the reaction mixture in the amidocarboxymethylation reaction zone can vary widely depending on the specific reactants and conditions employed. Typically, residence time can vary over the range of about 1 minute to about 500 minutes, preferably about 10 minutes to about 250 minutes, more preferably about 30 minutes to about 100 minutes. One skilled in the art can determine optimal residence times for a particular reactor configuration from the teachings herein.

B. Amidocarboxymethylation Catalyst Recovery

The amidocarboxymethylation catalyst is preferably recovered from the amidocarboxymethylation reaction product stream for reuse. In general, three approaches for catalyst recovery are presently preferred: a precipitation approach, a polymer or other solid support bed approach, and an extraction approach.

1. Polymer Or Other Solid Support Bed Approach

To recover the catalyst, the reaction product stream may be contacted with a bed of a polymeric or other solid material having a species bound thereto that will reversibly bind catalyst present in the reaction product stream. For example, the bed may comprise a triary or trialkyl phosphine species such as triphenyl phosphine supported on a cross-linked polystyrene or other suitable hydrocarbon polymer such as polybutadiene, or on an inorganic oxide support such as silica or alumina. Polystyrene supported phosphine species may be obtained commercially, for example, from Fluka Chemie (Milwaukee, Wis.) or prepared as generally described in Evans et al., *J. Org. Chem.* 67 (1974) 295–314. The polymer may contain, for example, about 3 mmoles of phosphine per gram of resin.

The supported phosphine species and reaction product mixture are contacted under conditions that permit, as near as is commercially practical, quantitative recovery of the catalyst. For example, the molar ratio of phosphine species to catalyst in the reaction product mixture will generally be about 1:1 to about 3:1, and preferably about 1.5:1 to about 2:1, respectively. The adsorption temperature will generally be about 50 to about 130° C., and preferably about 100 to about 120° C. The adsorption pressure will generally be about 20 to about 3200 psi (about 140 to about 22,000 kPa), preferably about 40 to about 2400 psi (about 275 to about 16,500 kPa), and more preferably about 50 to about 750 psi (about 350 to about 5,200 kPa). The atmosphere is preferably a carbon monoxide/hydrogen atmosphere with the partial pressure ratio of the two being about 95:5, respectively. The reaction product mixture is contacted with the bed for period sufficient to produce a solution containing a relatively small amount of catalyst, e.g., less than about 0.08 wt % and preferably less than about 0.015 wt %, and a relatively large amount of N-(acetyl)iminodiacetic acid, e.g., at least about 5 wt %, preferably at least about 15 wt. %, and more preferably at least about 20 wt %.

Upon completion of adsorption, the catalyst may be desorbed from the support by contacting the bed with a solution containing acetamide (or acetamide derivative) in a solvent such as THF, acetone or acetic acid. In general, the molar ratio of acetamide in the desorption solution to polymer bound catalyst is about 1:1 to about 1000:1, preferably about 5:1 to about 100:1. In addition, the desorption solution preferably contains at least about 3 wt % acetamide, more preferably at least about 6 wt % acetamide and most preferably about 10 wt % to about 30 wt % acetamide. The desorption temperature will preferably be about 170 to about 190° C., the desorption pressure will be at least about 2,000 psi, more preferably at least about 2,500 psi, and most preferably at the greatest pressure which is commercially practical. The operation is preferably carried out in a carbon monoxide/hydrogen atmosphere with the partial pressures of the two being about 95:5 to about 70:30, respectively. The resulting desorption product which comprises cobalt tetracarbonyl anion in a solvent may simply be returned to the amidocarboxymethylation reactor system since no regeneration is required.

The cobalt may alternatively be desorbed from the support by oxidizing the cobalt species on the support in the presence of an oxidizing agent such as oxygen, peroxide or proton, preferably at an elevated temperature (e.g., >100° C.) and a reduced pressure (e.g., <100 psi). The resulting oxidized species is soluble in a desorbing medium.

Instead of supported phosphines, the bed may be comprised of a cation or anion exhange species which reversibly binds the catalyst on a solid support, for example crosslinked polystyrene, polybutadiene, or an inorganic oxide such as silica or alumina. Such species include sulfonate, carboxylate, phosphate, alkylsulfonic acid, arylsulfonic acid, carboxylic acid, iminodiacetic acid, phosphonic acid, thiol, polyamine, alkylamine, arylamine, amide, pyridine, quaternary ammonium, quaternary alkylamine, quaternary alkylalkanolamine, and quaternary alkylbenzylamine species. In addition, the bed may comprise a mixture of these materials.

When ion exchange resins are used, cobalt species in the amidocarboxymethylation reaction product mixture are oxidized in the presence of an acid to Co(II). The acid employed for this purpose may be the polymer bound acid species of the ion exchange resin. Alternatively, an acid such as a mineral or organic acid may optionally be added to the reaction product mixture. To rapidly drive the oxidation to completion, the amidocarboxymethylation reaction product mixture is heated to a temperature of at least about 100° C. in the presence of the acid. Advantageously, the resulting Co(II) is bound to the resin and the resulting amidocarboxymethylation reaction product mixture contains a relatively small amount of catalyst, e.g., less than about 0.08 wt % and preferably less than about 0.015 wt %, and a relatively large amount of N-(acetyl)iminodiacetic acid, e.g., at least about 5 wt %, preferably at least about 15 wt. %, and more preferably at least about 20 wt %.

Upon completion of adsorption, the catalyst may be desorbed from the ion exchange resin by contacting the resin bed with a solution containing acetamide (or acetamide derivative) in a solvent such as THF, acetone or acetic acid. In general, the molar ratio of acetamide in the desorption solution to resin bound catalyst is about 1:1 to about 1000:1, preferably about 5:1 to about 100:1. In addition, the desorption solution preferably contains at least about 3 wt %, more preferably about 6 wt %, and most preferably about 10 wt % to about 30 wt % acetamide. The desorption temperature will preferably be about 70 to about 200° C., more preferably about 100 to about 130° C., the desorption pressure will be at least about 1,500 psi, more preferably at least about 3,000 psi, and most preferably as great as is commercially practical. The operation is preferably carried out in a carbon monoxide/hydrogen atmosphere with the partial pressures of the two being about 70:30 respectively. The resulting desorption product which comprises cobalt tetracarbonyl anion in a solvent may simply be returned to the amidocarboxymethylation reactor system since no regeneration is required.

Presently, it is preferred that multiple vessels be used to recover the catalyst from the amidocarboxymethylation reaction product stream and recycle it for reuse in the amidocarboxymethylation reactor system. For example, one or more vessels may be in the adsorption mode while one or more other vessels are in the desorption mode.

2. Precipitation Approach

In the precipitation approach for recovering catalyst from the amidocarboxymethylation reaction product stream, the catalyst is oxidized to form a precipitate which is then separated from the product stream. For example, cobalt tetracarbonyl anion in the reaction product stream may be oxidized to cobalt(II) oxalate by adding oxalic acid to the amidocarboxymethylation reaction product stream and heating the mixture to a temperature of about 100° C. for about 1 hour to cause the cobalt(II) oxalate to precipitate. The precipitate is separated from the product stream by any convenient means, for example, by filtration or centrifugation. The solid may then be calcined in a furnace to generate cobalt oxide, for example, at a temperature of about 300° C. to about 400° C. for a period of about 1 to about 3 hours. The resulting cobalt oxide can be suspended in a slurry with a solvent (e.g., THF, heptane, water or water/acetic acid mixtures), and regenerated. The resulting reaction product stream thus contains solvent, a relatively small amount of catalyst, e.g., less than about 0.08 wt % and preferably less than about 0.015 wt %, and a relatively large amount of N-(acetyl)iminodiacetic acid, e.g., at least about 5 wt %, preferably at least about 15 wt. %, and more preferably at least about 20 wt %.

Several methods for regenerating a cobalt catalyst have been reported in the literature which may be used in accordance with one aspect of the present invention. For example, in U.S. Pat. No. 4,954,466 Weisenfeld suggests converting a cobalt(II) precipitate to dicobaltoctacarbonyl by reacting the precipitate with carbon monoxide and hydrogen at a temperature of 150 to 180° C. with a pressure of 1500 to 6000 psi (10,345 to 41,380 kPa).

Another method for regenerating a amidocarboxymethylation cobalt catalyst is described in European Patent Application Publication No. EP 0 779 102 A1. In that method, cobalt hydroxide recovered from a amidocarboxymethylation reaction is introduced into the melt of an N-acyl amino acid derivative such as an N-acylsarcosine. The mixture is then added to a polar aprotic solvent and reacted with carbon monoxide or a mixture of carbon monoxide and hydrogen to form a amidocarboxymethylation catalytic mixture contains hydridocobalttetracarbonyl.

The rate of regeneration of the cobalt(II) salt can be dramatically increased if it is reacted with acetamide (or acetamide derivative) and/or an initially catalytic amount of a cobalt carbonyl species is added along with carbon monoxide and hydrogen. Advantageously, the product of this reaction is the base pair which participates in the amidocarboxymethylation step.

During regeneration, the reaction pressure generally ranges from at least about 200 psi to about 6,000 psi (1,400 to about 42,000 kPa), preferably from about 800 psi to about 3,700 psi (5,600 to about 26,000 kPa), and more preferably from about 1,500 psi to about 3,500 psi (10,500 to about 24,000 kPa). In general, the carbon monoxide-to-hydrogen partial pressure ratio during regeneration ranges from about 99:1 to about 1:99, preferably from about 30:70 to about 90:10, and more preferably from about 50:50 to about 75:25. The progress of the regeneration reaction can be followed by monitoring the uptake of gas, for example, by monitoring head pressure. During the regeneration step it is often advantageous to heat the reaction mixture. Typically, reaction mixture temperatures range from about 70° C. to about 170° C., preferably from about 90° C. to about 150° C., and more preferably from about 100° C. to about 140° C. Reaction times for the regeneration step can vary from about 1 minute to about 5 hours, preferably from about 5 minutes to about 2 hours, and more preferably from about 10 minutes to about 1 hour. If desired, the regeneration step can be performed in the presence of the organic acid co-catalyst used in the amidocarboxymethylation step. The regenerated active catalyst complex can, if desired, be used in a amidocarboxymethylation reaction directly after regeneration.

The anionic portion of the cobalt(II) salt is not critical to the regeneration step. For example, the cobalt(II) can be in the form of a salt of the conjugate base of the amidocarboxymethylation reaction product from which the cobalt(II) was recovered. Alternatively, the cobalt(II) can be in any other convenient form such as cobalt acetate, cobalt stearate, cobalt acetylacetonate, or cobalt oxalate and the hydrates thereof.

3. Extraction Approach

Cobalt compounds that are soluble in organic solvents, such as dicobalt octacarbonyl and hydridocobalt tetracarbonyl, can be recovered from the amidocarbonylation reaction product stream by extraction with an organic solvent that is substantially immiscible with water. Examples of such organic solvents include aromatics such as benzene and naphthalene, substituted aromatics such as toluene, xylenes, and anisole, alkanes such as pentanes, hexanes, heptanes, octanes, and substituted alkanes such as octanol, carbon tetrachloride, chloroform, methylene chloride, carbon disulfide, tetrachloroethylene, trichloroethylene, 1,1,1trichloroethane, 1,1,2-trichloroethane, cyclopentane, cyclopentene, diethylcarbonate, neopentane, pentane, 1-pentene, 2-pentene, trichlorobenzenes, o-dichlorobenzene, m-dichlorobenzene, p-dichlorobenzene, nitrobenzene, benzene, cyclohexane, hexane, hexenes, 2,2-dimethylbutane, 2,3-dimethylbutane, triethylphosphite, heptane, heptenes, benzonitrile, toluene, cycloheptane. Methylcyclohexane, ethylbenzene, m-xylene, o-xylene, p-xylene, octane, i-octane, nonane, decane, furan, decalin, methyl ethyl ether, diethyl ether, methyl isobutyl ether, and petroleum ether. The extraction can be performed under conditions that favor formation of organic soluble cobalt species. For example, performing the extraction in the presence of carbon monoxide can influence the proportion of dicobalt octacarbonyl recovered and the addition of acids or other adjuvants can increase extraction of hydridocobalt tetracarbonyl or the cobalt tetracarbonyl anion. Extraction of the amidocarbonylation reaction product stream can be accomplished in one or more real or theoretical stages in a co-current or counter-current fashion and with the optional introduction of additional water.

The aqueous liquid phase resulting from an extraction may contain a high concentration of N-(acetyl)iminodiacetic acid that will form crystals that can be recovered by filtration or centrifugation or the concentrated solution can be used in the phosphonomethylation reaction without isolation of N-(acetyl)iminodiacetic acid. Cobalt compounds may be removed from the organic phase by re-extraction, for example with an aqueous solution of acetamide, formaldehyde, or their equivalents, or by gas stripping where volatile cobalt (i.e., hydridocobalt tetracarbonyl) is removed (known in hydroformylation, e.g., W. H. Summerlin, U.S. Pat. No. 5,237,104) and absorbed, for example, into a solution of acetamide.

C. Phosphonomethylation

The product stream exiting the catalyst recovery system generally contains solvent, a relatively large amount of amidocarboxymethylation reaction products, mostly N-(acetyl)iminodiacetic acid, and a relatively small amount of catalyst. Before going into the phosphonomethylation reactor, solvent is preferably removed by distillation from the amidocarboxymethylation reaction product stream and returned to the amidocarboxymethylation reactor system. In general, it is desirable to obtain an N-(acetyl) iminodiacetic acid solution with as little solvent as is practical, preferably less than 1 wt % solvent, and most preferably less than 0.1 wt % solvent.

Miller et al. (U.S. Pat. No. 4,657,705) disclose a process in which substituted ureas, amides and carbamates are phosphonomethylated to produce an N-substituted aminomethylphosphonic acid which can be converted to glyphosate; in the disclosed process, the urea, amide or carbamate is (1) mixed with an aqueous acidic medium comprising phosphorous acid and an acid selected from among sulfuric, hydrochloric and hydrobromic acids and (2) heated to a temperature between about 70 and about 120° C. Phosphonomethylation reactions can also be carried out using phosphorous trichloride instead of phosphorous acid (for example, U.S. Pat. No. 4,400,330).

Jones et al. (U.S. Pat. No. 5,527,953) disclose a process for the manufacture of N-(phosphonomethyl)iminodiacetic acid from iminodiacetic acid which includes 1) reacting iminodiacetic acid with phosphorous acid and a source of formaldehye in aqueous solution in the presence of concentrated sulfuric acid (i.e., 0.5–2 moles of sulfuric acid per mole of iminodiacetic acid), 2) filtering and recovering the N-(phosphonomethyl)iminodiacetic acid product precipitated in the first stage, 3) recovering the filtrates from the second stage and optionally removing a proportion of water therefrom, 4) transferring the filtrates from the third stage to a further reaction stage in which further iminodiacetic acid is reacted with phosphorous acid and a source of formaldehyde in the presence of sulfuric acid, and thereafter 5) repeating stages one through four in a plurality of re-cycles.

1. N-(acetyl)iminodiacetic Acid Route

In general, the processes disclosed by Miller et al. and Jones et al. may be used to phosphonomethylate N-(acetyl) iminodiacetic acid. Typically, N-(acetyl)iminodiacetic acid is treated with a source of phosphorous and a source of formaldehyde. Another mineral acid such as sulfuric acid, a sulfonic acid such as methanesulfonic acid or toluenesulfonic acid, or hydrochloric acid is preferably added. Reaction temperatures generally range from about 80° C. to about 150° C., preferably from about 100° C. to about 140° C., more preferably from about 120° C. to about 140° C. Reaction times generally range from about 10 minutes to about 5 hours, preferably from about 20 minutes to about 3 hours, more preferably from about 30 minutes to about 2 hours. Any phosphorylating agent which provides a source of phosphorous acid or phosphorous acid equivalent can be used in the phosphonomethylation reaction. For example, phosphorous acid, phosphorous trichloride, phosphorous tribromide, phosphorous acid esters, chlorophosphonic acid and esters of chlorophosphonic acid can be used. Phosphorous acid and phosphorous trichloride are preferred. Formaldehyde can be derived from any source, for example, formalin (preferably 50%) or paraformaldehyde.

The phosphonomethylation results in the replacement of the N-acetyl substituent of N-(acetyl)iminodiacetic acid with an N-phosphonomethyl group to produce N-(phosphonomethyl)iminodiacetic acid which precipitates from the solution.

The phosphonomethylation reaction may be carried out in the batch or continuous mode. Preferably, it is carried out in the continuous mode. If carried out in the continuous mode, the process may optionally include 1) reacting N-(acetyl) iminodiacetic acid with phosphorous acid and a source of formaldehye in aqueous solution in the presence of an acid such as sulfuric acid, a sulfonic acid, hydrobromic acid or hydrochloric acid to form N-(phosphonomethyl) iminodiacetic acid and precipitating the N-(phosphonomethyl)iminodiacetic acid product in the presence of acetic acid, 2) filtering and recovering the N-(phosphonomethyl)iminodiacetic acid precipitate formed in the first stage, 3) recovering the filtrates from the second stage and optionally removing a proportion of water therefrom, 4) transferring the filtrates from the third stage to a further reaction stage in which further N-(acetyl)

iminodiacetic acid is reacted with a phosphorous source and a formaldehyde source in the presence of an acid such as sulfuric acid, a sulfonic acid, hydrobromic acid or hydrochloric acid, and thereafter 5) repeating stages one through four in a plurality of re-cycles.

2. Diketopiperazine Route

In the N-(acetyl)iminodiacetic acid route described above, the phosphonomethylation reaction results in the replacement of the N-acetyl substituent with an N-phosphonomethyl group to produce N-(phosphonomethyl)iminodiacetic acid. This reaction is shown generically in Scheme 4 wherein $R^1$ is methyl and $R^2$ is carboxymethyl.

Reaction Scheme 4

In another embodiment of the present invention, 2,5-diketopiperazines are phosphonomethylated with phosphorous trichloride, phosphorous acid, or a source of phosphorous acid in the presence of a source of formaldehyde to form N-(phosphonomethyl)iminodiacetic acid as shown in Reaction Scheme 4a.

Reaction Scheme 4a wherein $R^2$ and $R^{2a}$ are carboxymethyl or the salts or esters thereof. In general, the processes described above for phosphonomethylating N-(acetyl)iminodiacetic acid may be used to phosphonomethylate diketopiperazine.

The 2,5-diketopiperazines may be readily obtained by deacylating and cyclizing N-(acetyl)iminodiacetic acid in a single step as depicted in Reaction Scheme 2:

Reaction Scheme 2 wherein $R^2$ and $R^{2a}$ are carboxymethyl or the salts or esters thereof. Typically, reaction temperatures for formation of the diketopiperazines ranges from about 100° C. to about 250° C., preferably about 150° C. to about 220° C., more preferably about 185° C. to about 200° C. The reaction is relatively rapid, and reaction time typically ranges from about 1 minute to about 10 hours, preferably about 5 minutes to about 5 hours, still more preferably about 10 minutes to about 3 hours. The amount of added water measured as a percent of the starting material generally ranges up to about 85 wt. %, preferably from about 5 wt. % to about 70 wt. %, and more preferably from about 9 wt. % to about 20 wt. %. If desired, a catalyst can be added to the reaction mixture. Preferably, it is an organic acid and still more preferably it is a $C_1$ to about $C_3$ carboxylic acid. Most preferably, the acid catalyst is acetic acid. Solvents can optionally be present in the reaction mixture. For example, ethers, ketones, or nitrites can be added.

The formation of the 2,5-diketopiperazines from N-(acetyl)iminodiacetic acid may be advantageous for a number of reasons. As a general rule, they are less soluble in many solvents and in water than is the corresponding acid. As a result, the diketopiperazine can be more readily precipitated from the reaction mixture, separated, and handled. Furthermore, since the deacylation reaction does not require strong mineral acids, it is less corrosive to process equipment than a hydrolysis reaction in which strong mineral acids are employed.

D. N-(phosphonomethyl)iminodiacetic Acid Recovery

The phosphonomethylation reaction product which contains N-(phosphonomethyl)iminodiacetic acid, formaldehyde, solvent and other by-products is fed to a centrifuge or other suitable separation equipment to isolate N-(phosphonomethyl)iminodiacetic acid as a product.

Experimental evidence obtained to date suggests that the presence of acetic acid increases the isolated yield of N-(phosphonomethyl) iminodiacetic acid. Without being bound to any theory, acetic acid appears to decrease the solubility of N-(phosphonomethyl)iminodiacetic acid. Accordingly, the phosphonomethylation reaction product mixture preferably contains at least about 5 wt %, more preferably at least about 7 wt %, and still more preferably at least about 10 wt % acetic acid. In general, however, the phosphonomethylation reaction product mixture will contain less than 30 wt % acetic acid and typically will contain less than about 20 wt % acetic acid.

E. Acetic Acid Recovery

The stream exiting the centrifuge, i.e., the centrate stream, consists of N-(phosphonomethyl)iminodiacetic acid that did not precipitate in the isolation step, formaldehyde, phosphorous acid, acetic acid, iminodiacetic acid, and impurities such as hydroxymethylphosphonic acid, and N-(methyl) iminodiacetic acid. From this stream, a purge is taken to reduce the accumulation of such impurities circulating in the system.

Either prior or subsequent to the purge, the centrate stream is concentrated by distillation to remove a portion of acetic acid. The acetic acid depleted stream preferably contains no more than about 10 wt % acetic acid, and in some embodiments may contain no more than about 5 wt % acetic acid and is returned to the phosphonomethylation reactor system.

F. Acetamide Synthesis

The acetic acid enriched stream is fed to an acetamide synthesis reactor along with a source of ammonia, preferably anhydrous ammonia. The acetamide product may then be fed directly to the amidocarboxymethylation reactor system, or fed to the amidocarboxymethylation reactor system after first being reacted with formaldehyde to generate hydroxymethylacetamide or methylene bisacetamide, or used in the recovery and/or recycle of catalyst.

G. Glyphosate Synthesis

N-(phosphonomethyl)iminodiacetic acid which is isolated in the N-(phosphonomethyl)iminodiacetic acid step may be converted to N-(phosphonomethyl)glycine by any means which is known in the art. For example, the N-(phosphonomethyl)iminodiacetic acid may be oxidized to N-(phosphonomethyl)glycine using a carbon catalyst as described in Hershman U.S. Pat. No. 3,969,398. The carbon catalyst is preferably carbon prepared as described in Chou U.S. Pat. No. 4,624,937.

H. Acetamide Derivatives

Instead of starting with acetamide in the amidocarboxymethylation reaction, an acetamide derivative may be used. As used herein, acetamide derivatives include hydroxymethyl acetamide, methylene bisacetamide, and any other composition which, upon hydrolysis, yields acetamide or hydroxymethyl acetamide. Examples of acetamide equivalents include the following compositions:

XXV

VI

I. Definitions

The following definitions are provided in order to aid the reader in understanding the detailed description of the present invention:

"Glyphosate" means N-(phosphonomethyl)glycine in acid form or any of its salt or ester forms.

"Hydrocarbyl" means a group composed of carbon and hydrogen. This definition includes alkyl, alkenyl, and alkynyl groups which are each straight chain, branched chain, or cyclic hydrocarbons from one to about twenty carbons. Also included in this definition are aryl groups composed of carbon and hydrogen. Hydrocarbyl therefore includes, for example, methyl, ethyl, propyl, butyl, pentyl, hexyl, cyclopropyl, cyclobutyl, cyclopentyl, cyclohexyl, methylcyclopentyl, ethenyl, propenyl, butenyl, pentenyl, hexenyl, ethyne, propyne, butyne, pentyne, hexyne, phenyl, naphthyl, anthracenyl, benzyl, and isomers thereof.

"Substituted hydrocarbyl" means a hydrocarbyl group in which one or more hydrogen has been substituted with a heteroatom-containing group. Such substituent groups include, for example, halo, oxo, heterocycle, alkoxy, hydroxy, aryloxy, -NO$_2$, amino, alkylamino, or amido. When the substituent group is oxo, the substituted hydrocarbyl can be, for example, an acyl group.

"Heteroatom" means an atom of any element other than carbon or hydrogen which is capable of forming chemical bonds.

"Heterocycle" means a saturated or unsaturated mono- or multi-ring carbocycle wherein one or more carbon atoms is replaced by N, S, P, or O. This includes, for example, the following structures:

wherein Z, Z', Z", or Z"' is C, S, P, O, or N, with the proviso that one of Z, Z', Z", or Z"' is other than carbon, but is not O or S when attached to another Z atom by a double bond or when attached to another O or S atom. Furthermore, the optional substituents are understood to be attached to Z, Z', Z", or Z"' only when each is C. The point of attachment to the molecule of interest can be at the heteroatom or elsewhere within the ring.

"Halogen" or "halo" means a fluoro, chloro, bromo, or iodo group.

"Carboxymethyl" means a group containing a carboxylate moiety attached by the carboxylate carbon atom to a saturated carbon atom which in turn is attached to the molecule of interest.

"Amidocarboxymethylation catalyst" or "Carbonylation catalyst" means a catalyst which is useful in carbonylation reactions, and particularly in amidocarboxymethylation reactions.

"Amidocarboxymethylation" means the introduction of a substituted or unsubstituted carboxymethyl group into the molecule of interest.

"PM" means phosphonomethylation.
"GC" means gas chromatography.
"HPLC" means high pressure liquid chromatography.
"IC" means ion chromatography.
"NMR" means nuclear magnetic resonance spectroscopy.
"MS" means mass spectrometry.

The following examples will illustrate the invention.

EXAMPLES

General: Yields of carbonylation products where determined by HPLC analysis. N-Acetyliminodiacetic acid (NAIDA) was quantified by ion exchange separation followed by UV detection. Standards were prepared containing 25 ppm to 250 ppm NAIDA in water and samples were diluted to fall within the calibration range. An Alltech Adsorbosphere XL SAX columns was used in this analysis with the following conditions. In the case of Example 13, an internal standard, was used to quantify product yields.

Mobile Phase: 0.0062 M KH$_2$PO$_4$+4% MeOH Adjust to pH 2.0 with 85% H$_3$PO$_4$ Column Flow Rate: 1.3 mL/min Column Temperature: Ambient Detector Wavelength: 195 nm Sample Loop: 50 ul Run Time: 20 minutes N-Acetylglycine (NAG) and hydroxymethylacetamide (HMA) were quantified by an ion exclusion separation followed by UV detection. Standards were prepared containing 25 ppm to 300 ppm HMA and 30 ppm to 500 ppm NAG in water. An Interaction Chemicals, Inc. ION-310 HPLC column was employed for this analysis using the following conditions. In the case of example 13, an internal standard was used to quantify yields.

Mobile Phase: 1 mL concentrated H$_2$SO$_4$ in 1 Liter of water

Column Flow Rate: 0.5 mL/min

Column Temperature: 32° C.
Detector Wavelength: 210 nm
Sample Loop: 30 ul
Run Time: 30 minutes Example 1

This example illustrates the carbonylation of acetamide in a continuous reaction system.

The general design of the continuous reaction system is shown in FIG. 1. The apparatus consisted of three 1 liter stirred autoclaves with a fixed liquid volume (450 mL at 1000 rpm and 350 mL at 2000 rpm) with a per stage residence time equal to total liquid flow divided by reactor volume. The third stage terminated into a five gallon autoclave that functioned as a high pressure liquid/gas separator. The separated gas was sent through a condenser followed by a high pressure caustic scrubbers (350 mL of 50% NaOH) before the back pressure regulator and exit line to the outside atmosphere. Solutions of acetamide/solvent/HOAc, 48 WT % formalin, and cobalt octacarbonyl ($Co_2(CO)_8$) or hydridocobalt tetracarbonyl ($HCo(CO)_4$) were individually pumped into stage 1 of the system by a high pressure 500D continuos flow ISCO pumps. Also being fed to the first stage CMA reactor was 3200 psi CO or $CO/H_2$ mixtures through a 10 SLLM Brooks flow controller. This gas originated in four 4 liter high pressure reservoirs that were maintained between 3500 and 4200 psi. The results of the operation of this reaction system are summarized below.

A) Reactions using Cobalt(II) acetate as precursor to hydridocobalt tetracarbonyl ($HCo(CO)_4$ as catalyst.

A 12 L round bottom flask was charged with $Co(OAc)_2 \cdot 4H_2O$ and glacial acetic acid to make a solution that was 7% by weight in cobalt metal. This suspension was heated to 75 degrees and was allowed to stir until the mixture became a homogeneous solution. This mixture was transferred at 75° C. within 0.5 h to a 1 gallon stirred autoclave. A longer hold period and insoluble Co(II) salts precipitated that would marginally dissolve in water. Higher temperatures or longer holds times caused a greater amount of this cobalt salt to form. Once in the 1 gallon autoclave, this cobalt/acetic acid solution was heated under 3200 psi $CO:H_2$ (70:30) at 130° C. until conversion to carbonyl had occurred which was evident by rapid uptake of gas. This stream was transferred under high pressure to a heat traced 500D continuous delivery ISCO pump system for feed into the first stage of the reaction system. A 22 liter flask containing approximately 14.5 WT % acetamide, 4 WT % HOAc, and 72.5% acetone were pumped with a 250 mL/min piston diaphragm pump to the high pressure 500D ISCO pump unit for delivery to the first stage of the reaction system. Under these conditions, the acetamide stream was a solution at room temperature. The 48 Wt % formalin was maintained at 75° C. and was gravity fed to the high pressure 500D ISCO pump for delivery into the first stage of the reaction system. The reactors were maintained at 110° C. and were stirred at 1000 rpm.

| Components | Flow Rates mL/min |
|---|---|
| Acetamide/Acetone/Acetic Acid Mixture | 33.87 |
| 48% Formalin | 9.66 |
| $HCo(CO)_4$/Acetic Acid | 6.47 |
| $CO:H_2$ (95:5) | 6.0 (L/min) |

Graph 1. Results of carbonylation of acetamide in continuous reaction system using Co(II)acetate catalyst precursor.

B) Reactions Using $Co_2(CO)_8$ as the catalyst feed.

Under an Argon atmosphere 300 g of $Co_2(CO)_8$ (95%) (Strem Chemicals Inc.) and 1500 mL of THF was charged into a 5 liter high pressure glass reactor and was placed under 25 psi CO at room temperature. This cobalt stream was fed by the positive CO pressure into the high pressure continuous delivery 500D ISCO pumps for metering into the first stage of the reaction system. The acetamide feed composed of 14.5% Acetamide, 4% glacial acetic acid in THF and the formalin feed was 48% in water stabilized with 1% methanol). Pressure was maintained at 3200 psig in all stages via a back flow regulator and the gas flow was 6 L/min of a 95:5 $CO:H_2$ composition. The results of these experiments are summarized in Table 2.

TABLE 2

| Run # | Elapsed Time (h:min) | Stage | Temp (° C.) | Stir Rate rpm | Feeds mL/min Stage 1 | | | Yields[1] Normalized Mole % | | |
|---|---|---|---|---|---|---|---|---|---|---|
| | | | | | Amide | $CH_2O$ | $Co_2(CO)_8$ | NAIDA | NAG | HMA |
| 1 | 0:58 | 1 | 100 | 1000 | 34.4 | 8.9 | 6.7 | 81 | 15 | 4 |
| | 1:08 | 2 | 100 | 1000 | | | | 87.5 | 11 | 1.5 |
| | 1:14 | 3 | 100 | 1000 | | | | 91 | 8 | 1 |
| | 1:56 | 1 | 100 | 1000 | | | | 78 | 18 | 4 |
| | 2:05 | 2 | 100 | 1000 | | | | 89 | 11 | 0 |
| | 2:15 | 3 | 100 | 1000 | | | | 94 | 6 | 0 |
| 2 | 1:03 | 1 | 100 | 2000 | 34.4 | 8.9 | 6.7 | 84 | 16 | 0 |
| | 1:18 | 2 | 100 | 2000 | | | | 93 | 7 | 0 |
| | 1:26 | 3 | 100 | 1000 | | | | 97 | 3 | 0 |
| | 2:03 | 1 | 100 | 2000 | | | | 86 | 14 | |

TABLE 2-continued

| Run # | Elapsed Time (h:min) | Stage | Temp (° C.) | Stir Rate rpm | Feeds mL/min Stage 1 Amide | $CH_2O$ | $Co_2(CO)_8$ | Yields[1] Normalized Mole % NAIDA | NAG | HMA |
|---|---|---|---|---|---|---|---|---|---|---|
| | 2:07 | 2 | 100 | 2000 | | | | 94 | 6 | |
| | 2:12 | 3 | 100 | 1000 | | | | 98 | 2 | |
| 3 | 1:06 | 1 | 100 | 1000 | 16.8 | 4.6 | 3.5 | 85 | 13 | 2 |
| | 1:13 | 2 | 100 | 1000 | | | | 91 | 9 | |
| | 1:21 | 3 | 100 | 1000 | | | | 91 | 9 | |
| | 1:56 | 1 | 100 | 1000 | | | | 86 | 12 | |
| | 2:00 | 2 | 100 | 1000 | | | | 94 | 6 | |
| | 2:05 | 3 | 100 | 1000 | | | | 97 | 3 | |
| | 2:58 | 1 | 100 | 1000 | | | | 90 | 8 | |
| | 3:03 | 2 | 100 | 1000 | | | | 95 | 5 | |
| | 3:08 | 3 | 100 | 1000 | | | | 98 | 2 | |
| | 5:56 | 1 | 100 | 1000 | | | | 85 | 13 | |
| | 6:01 | 2 | 100 | 1000 | | | | 94 | 6 | |
| | 6:04 | 3 | 100 | 1000 | | | | 98 | 2 | |
| 4 | 2:11 | 1 | 100 | 1000 | 8.4 | 2.3 | 1.7 | 86 | 12 | 2 |
| | 2:17 | 2 | 100 | 1000 | | | | 93 | 7 | 0 |
| | 2:22 | 3 | 100 | 1000 | | | | 91 | 9 | 0 |
| | 5:09 | 1 | 100 | 1000 | | | | 86 | 12 | 2 |
| | 5:13 | 2 | 100 | 1000 | | | | 95 | 5 | 0 |
| | 5:17 | 3 | 100 | 1000 | | | | 96 | 4 | 0 |
| | 8:10 | 1 | 100 | 1000 | | | | 86 | 12 | 2 |
| | 8:15 | 2 | 100 | 1000 | | | | 94 | 6 | 0 |
| | 8:20 | 3 | 100 | 1000 | | | | 95 | 5 | 0 |
| | 12:13 | 1 | 100 | 1000 | | | | 88 | 12 | 0 |
| | 12:18 | 2 | 100 | 1000 | | | | 94 | 6 | 0 |
| | 12:24 | 3 | 100 | 1000 | | | | 96 | 4 | 0 |
| 5 | 0:59 | 1 | 100 | 2000 | 33.6 | 9.7 | 6.5 | 87 | 11 | 2 |
| | 1:03 | 2 | 100 | 2000 | | | | 97 | 3 | 0 |
| | 1:07 | 3 | 100 | 1000 | | | | 97 | 3 | 0 |
| | 1:59 | 1 | 100 | 2000 | | | | 87 | 11 | 2 |
| | 2:07 | 2 | 100 | 2000 | | | | 97 | 3 | 0 |
| | 2:12 | 3 | 100 | 1000 | | | | 99 | 1 | 0 |
| 6 | 1:56 | 1 | 117 | 2000 | 33.87 | 9.7 | 6.5 | 86 | 11 | 3 |
| | 2:02 | 2 | 100 | 2000 | | | | 93 | 5 | 2 |
| | 2:06 | 3 | 100 | 1000 | | | | 95 | 3 | 2 |
| | 3:20 | 1 | 117 | 2000 | | | | 86 | 11 | 3 |
| | 3:28 | 2 | 100 | 2000 | | | | 92 | 5 | 3 |
| | 3:33 | 3 | 100 | 1000 | | | | 96 | 2 | 2 |
| | 4:26 | 1 | 118 | 2000 | | | | 85 | 11 | 4 |
| | 4:30 | 2 | 100 | 2000 | | | | 91 | 6 | 3 |
| | 4:34 | 3 | 100 | 1000 | | | | 94 | 3 | 3 |

Example 2

This example illustrates cobalt catalyst recovery from the carboxymethylation reaction using a phosphine supported polymer.

A 300 mL autoclave equipped with an overhead vortex stirrer was loaded with acetamide (11.90 g, 0.202 mol), paraformaldehyde (13.57 g, 0.45 mol), water (12.97 g, 0.72 mol), acetic acid (4.22 g, 0.070 mol), $Co_2(CO)_8$ (4.085 g, 0.0120 mol), and 90 mL THF. The autoclave was pressurized to 3177 psi 95/5 $CO/H_2$ and heated at 120° C. for 1 hour. The product stream of this reaction was then transferred through a dip tube and into a second 300 mL autoclave, initially at ambient temperature, containing triphenylphosphine supported on crosslinked polystyrene (9.931 g, 0.0318 mol P). The adsorption was carried out at 100° C. for 30 minutes under 3197 psi 95/5 $CO/H_2$. The color of the decobalted solution was light yellow and cobalt analysis determined that the solution contained 1228 ppm of cobalt, which is 18.2% of the total amount of cobalt originally charged. The color of the resin was dark red and the cobalt analysis showed that the resin contained 8.66 wt % cobalt, which is 77.8% of the total amount originally charged. Similar adsorption experiments were carried out and the results are summarized in Table 2.

TABLE 2

| Adsorption Conditions | | | | % Cobalt |
|---|---|---|---|---|
| mmol Co/ mmol P | Temperature (° C.) | Ratio of $CO/H_2$ | Pressure (psi) | remaining in solution |
| 0.73 | 23 | 95/5 | 3160 | 81.6% |
| 0.73 | 60 | 95/5 | 3160 | 49.0% |
| 0.75 | 100 | 95/5 | 3197 | 18.2% |
| 0.75 | 120 | 95/5 | 3160 | 14.3% |
| 0.74 | 100 | 95/5 | 126 | 13.2% |
| 0.74 | 100 | 95/5 | 53 | 5.2% |
| 0.63 | 100 | 95/5 | 2460 | 9.6% |
| 0.61 | 100 | 95/5 | 745 | 9.6% |
| 0.50 | 100 | 95/5 | 3126 | 11.4% |
| 0.61 | 100 | 100/0 | 3190 | 13.2% |
| 0.57 | 120 | 50/50 | 3185 | 12.9% |
| 0.59 | 120 | 95/5 | 3210 | 6.4%[a] |
| 0.61 | 120 | 95/5 | 3145 | 7.0%[b] |

[a] The carboxymethylation reaction was run with 22% less $H_2O$
[b] The carboxymethylation reaction was run with 40% less $H_2O$ As seen in Table 2, temperatures in the range of 100–120° C. gave superior adsorption of cobalt. In addition, lowering the pressure of $CO/H_2$ and decreasing the ratio of cobalt/ phosphorus improved the adsorption of cobalt on the phosphine resin. Gas composition had little effect on the properties of adsorption, but decreasing the water content of the carboxymethylation reaction further improved the removal of cobalt from solution. These runs demonstrate the feasibility of utilizing a triphenylphosphine resin to decobalt carboxymethylation product streams.

Example 3

This example illustrates the desorption of cobalt catalyst from a phosphine resin using solutions of acetamide under various conditions.

In a typical run, a 300 mL autoclave with an overhead vortex stirrer was loaded with acetamide (11.81 g, 0.200 mol), paraformaldehyde (13.63 g, 0.454 mol), water (12.93 g, 0.72 mol), acetic acid (4.25 g, 0.071 mol), $Co_2(CO)_8$ (4.043 g, 0.0118 mol), and 90 mL THF. The autoclave was pressurized to 3272 psi 95/5 $CO/H_2$ and heated at 120° C. for 30 min. The product stream of this reaction was then transferred through a dip tube into a second 300 mL autoclave containing triphenylphosphine supported on crosslinked polystyrene (9.997 g, 0.032 mol P) and 40 mL of THF. The adsorption was carried out at 100° C. for 30 minutes under 53 psi 95/5 $CO/H_2$. The solution was then removed from the autoclave via a fritted dip tube, leaving the resin in the autoclave. The decobalted solution was light orange-yellow and cobalt analysis determined that the solution contained 311 ppm of cobalt, which is 5.2% of the total amount of cobalt originally charged. A desorption solution of THF (90 mL) and acetamide (20.134 g, 0.341 mol) was pumped into the autoclave onto the cobalt-containing resin. The autoclave was pressurized to 3185 psi 95/5 $CO/H_2$ and heated to 190° C. After one hour of desorption, the solution was found to contain 4779 ppm cobalt, which is 63% of the amount of cobalt calculated to be initially adsorbed on the resin. Table 3 summarizes desorption data obtained from similar desorption runs.

TABLE 3

| Co on 10 g resin[a] | mol acetamide/ mol Co | Desorption Conditions | | | | % Co Desorbed[b] |
| --- | --- | --- | --- | --- | --- | --- |
| | | Ratio of $CO/H_2$ | Pressure (psi) | Temperature | Time | |
| 0.72 g | 16.4 | 95/5 | 3160 | 190 | 30 min | 24% |
| 0.77 g | 15.1 | 95/5 | 3130 | 190 | 1 hr | 25% |
| 0.92 g | 12.9 | 95/5 | 3090 | 190 | 1 hr | 37% |
| 1.14 g | 17.7 | 95/5 | 2730 | 190 | 1 hr | 47% |
| 1.322 g | 15.2 | 95/5 | 3185 | 190 | 1 hr | 63% |
| 0.891 g | 13.2 | 100/0 | 3230 | 190 | 1 hr | 14.9% |
| 0.947 g | 12.5 | 70/30 | 3210 | 190 | 1 hr | 51.7% |
| 0.978 g | 12.1 | 50/50 | 3214 | 190 | 1 hr | 43.4% |

[a]Expressed as grams Co metal per 10 grams resin. The amount of cobalt was calculated from the total charge to the carboxymethylation minus the amount of cobalt not removed during the adsorption step
[b]The percent cobalt desorbed is based on the amount calculated to be absorpbed initially onto the triphenylphosphine resin Example 4

This example illustrates the adsorption of cobalt from carboxymethylation product streams using a resin contained in a continuous flow column.

A 300 mL autoclave equipped with an overhead vortex stirrer was loaded with acetamide (11.87 g, 0.201 mol), paraformaldehyde (13.64 g, 0.454 mol), water (12.92 g, 0.72 mol), acetic acid (4.22 g, 0.070 mol), $Co_2(CO)_8$ (4.020 g, 0.0118 mol), and 90 mL THF. The autoclave was pressurized to 3246 psi 95/5 $CO/H_2$ and heated at 110° C. for 40 minutes. The product stream was removed from the autoclave and pumped through a column filled with triphenylphosphine supported on crosslinked polystyrene (11.36 g, 0.034 mol P). The adsorption was carried out at 2500 psi 95/5 $CO/H_2$, 100° C. with a flow rate of 2.5 mL/min through the resin bed. The color of the decobalted solution was light orange and cobalt analysis determined that the solution contained 589 ppm of cobalt, which is 6.7% of the total amount of cobalt originally charged. A second adsorption was then similarly carried out on the same batch of resin in the column bed. Table 4 contains the data for similar adsorption experiments.

TABLE 4

| Resin Batch # | Run Number | grams Co metal pre-column | grams Co metal post-column | % Co remaining |
| --- | --- | --- | --- | --- |
| 1 | 1 | 0.69 | 0.026 | 3.8% |
| 1 | 2 | 0.65 | 0.049 | 7.6% |
| 2 | 1 | 1.386 | 0.093 | 6.7% |
| 2 | 2 | 1.417 | 0.168 | 11.8% |
| 3 | 1 | 1.723 | 0.126 | 7.3% |

High adsorptions of cobalt were obtained using these conditions, even upon performing a second adsorption on the same resin bed. These runs demonstrate the feasibility of utilizing a triphenylphosphine resin in a continuous flow bed to decobalt carboxymethylation product streams.

Example 5

This example illustrate the recovery and regeneration of cobalt from a carboxymethylation reaction stream.

A mixture of acetamide (11.8 g, 200 mmol), paraformaldehyde (13.6 g, 450 mmol), dicobalt octacarbonyl (2 g, 6 mmol), acetic acid (4 g), water (13 mL), and THF (90 mL) was heated to 110° C. while applying rapid mechanical agitation and maintaining 3200 psi with a 95:5 $CO/H_2$ gas mixture. After about 30 min, the product mixture was cooled to about 35° C. and the pressure was vented to 100 psig. A solution of oxalic acid dihydrate (1.8 g, 14 mmol) in THF (20 mL) then was pumped into the autoclave and the mixture was heated to 110° C. After 60 min at 110° C., analysis of the filtered mixture revealed over 98% of the cobalt had precipitated as the oxalate salt.

Cobalt oxalate dihydrate (182.98 g, 1.00 mol) was calcined in air in a muffle furnace at 350° C. for 1.5 hr to afford 75.4 g of a black solid that gained mass upon cooling overnight to room temperature to leave 80.3 g of a black solid.

A portion of the cobalt oxide prepared above (54.0 g, 0.673 mol) was placed in a 2-L Hastelloy-C autoclave containing 1 L of THF. The mixture was heated to 150° C. under 3400 psi of a 70/30 mixture of $CO/H_2$ with rapid mechanical agitation. Within about 10 min of reaching 150° C., rapid gas uptake was noted and a modest exotherm (~10° C.) was recorded. FTIR spectroscopy revealed large absorbances corresponding to $Co_2(CO)_8$ and $[Co(CO)_4]^-$. The mixture continued to stir at 140–150° C. at about 3400 psi for 6 hr. After cooling to 25° C. and reducing the pressure to about 1000 psig, the liquid mixture was discharged from the reactor via a sample line fitted with a metal fritted filter. The dark brown solution, 972.5 g, was found to contain about 3.8 wt % cobalt consistent with 92% of that expected based upon the cobalt oxide (as $Co_3O_4$) charged. Examination of the reactor contents after complete removal of liquid found no solids remaining.

Example 6

This example illustrates the preparation of N-(phosphonomethyl)iminodiacetic acid from a typical carboxymethylation reaction mixture with recycle of the filtrate.

A typical carboxymethylation reaction mixture was sparged with air, then was concentrated to remove the solvent. To remove cobalt the mixture was treated with oxalic acid and filtered. The filtrate was further concentrated to a concentration of 0.4334 moles of N-acetyliminodiacetic acid plus iminodiacetic acid per 100 g.

A) Cycle 1: A 500-mL glass pressure reactor (Ace Glass Co.) was charged with the above carbonylation reaction mixture (88.5 g), water (40 g), acetic acid (24 g), phosphorous acid (39.4 g) and 12 N HCl (68 g). The mixture was heated to 120° C. and 43.7% formaldehyde (31.4 mL) was added drop wise over a one hour period. After another ½ hour at 120° C. the mixture was cooled by distillation at reduced pressure and stirred at 35° C. for two hours. The mixture was filtered and the solid was washed with water to give 58.1 g of N-(phosphonomethyl)iminodiacetic acid.

B) Cycle 2: The combined filtrate and wash from cycle 1 was concentrated to 65 g. A 500-mL pressure reactor was charged with the concentrate (65 g), the carbonylation reaction mixture (88.5 g), water (20 g), acetic acid (12 g), phosphorous acid (39.4 g) and 12 N HCl (55 g). The mixture was heated to 120° C. and 43.7% formaldehyde (31.4 mL) was added drop wise over a one hour period. After another ½ hour at 120° C. the mixture was cooled by distillation at reduced pressure and stirred at 45° C. for two hours. The mixture was filtered and the solid was washed with water to give 75.1 g of N-(phosphonomethyl)iminodiacetic acid.

C) Cycle 3: The combined filtrate and wash from cycle 2 was concentrated to 149 g. A 500-mL pressure reactor was charged with the concentrate (149 g), the carbonylation reaction mixture (92.2), phosphorous acid (32.8 g) and 12 N HCl (50 g). The mixture was heated to 120° C. and 43.7% formaldehyde (31.4 mL) was added drop wise over a one hour period. After another ½ hour at 120° C. the mixture was cooled by distillation at reduced pressure and stirred at 45° C. for two hours. The mixture was filtered and the solid was washed with water to give 80.6 g of N-(phosphonomethyl)iminodiacetic acid.

D) Cycle 4: The combined filtrate and wash from cycle 3 was concentrated to 110 g. A 500-mL pressure reactor was charged with the concentrate (110 g), the carbonylation reaction mixture (88.5 g), phosphorous acid (39.4 g), water (50 g) and 12 N HCl (50 g). The mixture was heated to 120° C. and 47.0% formaldehyde (31.4 mL) was added drop wise over a one hour period. After another ½ hour at 120° C. the mixture was cooled by distillation at reduced pressure and stirred at 45° C. for two hours. The mixture was filtered and the solid was washed with water to give 85.9 g of N-(phosphonomethyl)iminodiacetic acid.

Example 7

This example illustrates the preparation of N-(phosphonomethyl)iminodiacetic acid from 1,4-di(carboxymethyl)-2,5diketopiperazine with recycle of the filtrate using sulfuric acid catalyst.

A) Cycle 1: A pressure reactor was charged with 1,4-di(carboxymethyl)-2,5diketopiperazine (9.21 g), water (6.99 g) phosphorous acid (8.22 g) and 98% sulfuric acid (13.3 g). The mixture was heated to 130° C. and 43.7% formaldehyde (5.0 mL) was added drop wise over a one hour period. After another ½ hour at 130° C. the mixture was cooled to 30° C. The mixture was filtered and the solid was washed with water to give 13.0 g of N-(phosphonomethyl)iminodiacetic acid.

B) Cycle 2: The filtrate and wash from cycle 1 was concentrated. A pressure reactor was charged with the concentrated filtrate, 1,4-di(carboxymethyl)-2,5diketopiperazine (9.22 g), water (1.46 g), phosphorous acid (8.10 g) and 98% sulfuric acid (5.5 g). The mixture was heated to 130° C. and 43.7% formaldehyde (5.0 mL) was added drop wise over a one hour period. After another ½ hour at 130° C. the mixture was cooled to 30° C. and water (15 mL) was added. The mixture was filtered and the solid was washed with water to give 10.15 g of N-(phosphonomethyl)iminodiacetic acid.

C) Cycle 3: The filtrate and wash from cycle 2 was concentrated. A pressure reactor was charged with the concentrated filtrate, 1,4-di(carboxymethyl)-2,5-diketopiperazine (9.21 g), water (7.00 g), phosphorous acid (6.56 g) and 98% sulfuric acid (8.03 g). The mixture was heated to 130° C. and 43.7% formaldehyde (5.0 mL) was added drop wise over a one hour period. After another ½ hour at 130° C. the mixture was cooled to 30°. The mixture was filtered and the solid was washed with water to give 9.49 g of N-(phosphonomethyl)iminodiacetic acid.

Example 8

This example illustrates the preparation of N-(phosphonomethyl)iminodiacetic acid from 1,4-di(carboxymethyl)-2,5diketopiperazine with recycle of the filtrate using hydrochloric acid catalyst.

A) Cycle 1: A pressure reactor was charged with 1,4-di(carboxymethyl)-2,5diketopiperazine (9.20 g), water (7.05 g) phosphorous acid (8.20 g) and 12 N hydrochloric acid (12.03 g). The mixture was heated to 130° C. and 43.7% formaldehyde (5.0 mL) was added drop wise over a one hour period. After another ½ hour at 130° C. the mixture was cooled to 30° C. The mixture was filtered and the solid was washed with water to give 10.30 g of N-(phosphonomethyl)iminodiacetic acid.

B) Cycle 2: The filtrate and wash from cycle 1 was concentrated. A pressure reactor was charged with the concentrated filtrate, 1,4-di(carboxymethyl)-2,5diketopiperazine (9.20 g), water (1.48 g) phosphorous acid (6.63 g) and 12 N hydrochloric acid (7.69 g). The mixture was heated to 130° C. and 43.7% formaldehyde (5.0 mL) was added drop wise over a one hour period. After another ½ hour at 130° C. the mixture was cooled to 30° C. The mixture was filtered and the solid was washed with water to give 9.33 g of N-(phosphonomethyl)iminodiacetic acid.

C) Cycle 3: The filtrate and wash from cycle 2 was concentrated. A pressure reactor was charged with the concentrated filtrate, 1,4-di(carboxymethyl)-2,5-diketopiperazine (9.20 g), water (7.02 g) phosphorous acid (6.56 g) and 12 N hydrochloric acid (7.69 g). The mixture was heated to 130° C. and 43.7% formaldehyde (5.0 mL) was added drop wise over a one hour period. After another ½ hour at 130° C. the mixture was cooled to 30° C. The mixture was filtered and the solid was washed with water to give 10.7 g of N-(phosphonomethyl)iminodiacetic acid.

D) Cycle 4: The filtrate and wash from cycle 3 was concentrated. A pressure reactor was charged with the concentrated filtrate, 1,4-di(carboxymethyl)-2,5diketopiperazine (9.20 g), water (7.00 g) phosphorous acid (6.56 g) and 12 N hydrochloric acid (7.67 g). The mixture was heated to 130° C. and 43.7% formaldehyde (5.0 mL) was added drop wise over a one hour period. After another ½ hour at 130° C. the mixture was cooled to 30° C. The mixture was filtered and the solid was washed with water to give 9.7 g of N-(phosphonomethyl)iminodiacetic acid.

Example 9

This example illustrates the preparation of N-(phosphonomethyl)iminodiacetic acid from N-acetyliminodiacetic acid with recycle of the filtrate and use of phosphorus trichloride to provide makeup HCl and phosphorous acid.

A) Cycle 1: A pressure reactor was charged N-acetyliminodiacetic acid (XVI) monohydrate (15.21 g), water (7.00 g) phosphorous acid (8.12 g) and 12 N HCl (12.00 g). The mixture was heated to 120° C. and 43.7% formaldehyde (4.75 mL) was added drop wise over a one hour period. After another ½ hour at 120° C. the mixture was cooled to 30° C. The mixture was filtered and the solid was washed with water to give 13.63 g of N-(phosphonomethyl)iminodiacetic acid.

B) Cycle 2: The filtrate and wash from cycle 1 was concentrated. A pressure reactor was charged with the concentrate from cycle 1, N-acetyliminodiacetic acid monohydrate (13.68 g), water (7.07 g) phosphorous acid (3.41). Phosphorus trichloride (2.72 mL) was added to the mixture drop wise. The mixture was heated to 120° C. and 43.7% formaldehyde (5.0 mL) was added drop wise over a one hour period. After another ½ hour at 120° C. the mixture was cooled to 30° C. The mixture was filtered and the solid was washed with water to give 10.69 g of N-(phosphonomethyl)iminodiacetic acid.

C) Cycle 3: The filtrate and wash from cycle 2 was concentrated. A pressure reactor was charged the concentrate from cycle 2, N-acetyliminodiacetic acid monohydrate (13.68 g), water (7.07 g) phosphorous acid (3.41). Phosphorus trichloride (2.72 mL) was added to the mixture drop wise. The mixture was heated to 120° C. and 47.0% formaldehyde (5.0 mL) was added drop wise over a one hour period. After another ½ hour at 120° C. the mixture was cooled to 30° C. The mixture was filtered and the solid was washed with water to give 11.60 g of N-(phosphonomethyl)iminodiacetic acid.

D) Cycle 4: The filtrate and wash from cycle 3 was concentrated. A pressure reactor was charged the concentrate from cycle 3, N-acetyliminodiacetic acid monohydrate (13.69 g), water (8.07 g) phosphorous acid (3.41). Phosphorus trichloride (2.72 mL) was added to the mixture drop wise. The mixture was heated to 120° C. and 47.0% formaldehyde (5.0 mL) was added drop wise over a one hour period. After another ½ hour at 120° C. the mixture was cooled to 30° C. The mixture was filtered and the solid was washed with water to give 11.19 g of N-(phosphonomethyl)iminodiacetic acid.

E) Cycle 5: The filtrate and wash from cycle 4 was concentrated. A pressure reactor was charged the concentrate from cycle 4, N-acetyliminodiacetic acid monohydrate (13.68 g), water (7.07 g) phosphorous acid (3.41). Phosphorus trichloride (2.72 mL) was added to the mixture drop wise. The mixture was heated to 120° C. and 47.0% formaldehyde (5.0 mL) was added drop wise over a one hour period. After another ½ hour at 120° C. the mixture was cooled to 30° C. The mixture was filtered and the solid was washed with water to give 13.21 g of N-(phosphonomethyl)iminodiacetic acid.

F) Cycle 6: The filtrate and wash from cycle 5 was concentrated. A pressure reactor was charged the concentrate from cycle 5, N-acetyliminodiacetic acid monohydrate (13.68 g), water (7.07 g) phosphorous acid (3.41). Phosphorus trichloride (2.72 mL) was added to the mixture drop wise. The mixture was heated to 120° C. and 47.0% formaldehyde (5.0 mL) was added drop wise over a one hour period. After another ½ hour at 120° C. the mixture was cooled to 30° C. The mixture was filtered and the solid was washed with water to give 12.11 g of N-(phosphonomethyl)iminodiacetic acid.

Example 10

This example illustrates the preparation of N-(phosphonomethyl)iminodiacetic acid from N-acetyliminodiacetic acid with recycle of the filtrate using sulfuric acid catalyst.

A) Cycle 1: A reactor was charged with N-acetyliminodiacetic acid monohydrate (1 7.0 g), water (5 g), phosphorous acid (11.39 g) and 98% sulfuric acid (15 g). The mixture was heated to 110° C. and 42.2% formaldehyde (5.6 mL) was added drop wise over a one hour period. After another 1¾ hour at 110° C. the mixture was cooled to 25° C. The mixture was filtered and the solid was washed with water to give 12.46 g of N-(phosphonomethyl)iminodiacetic acid.

B) Cycle 2: The filtrate and wash from cycle 1 was concentrated. A reactor was charged with the concentrate from cycle 1, N-acetyliminodiacetic acid monohydrate (19.0 g), phosphorous acid (8.2 g). The mixture was heated to 110° C. and 42.2% formaldehyde (4.9 mL) was added drop wise over a one hour period. After another 1¾ hour at 110° C. the mixture was cooled to 25° C. The mixture was filtered and the solid was washed with water to give 21.8 g of N-(phosphonomethyl)iminodiacetic acid.

C) Cycle 3: The filtrate and wash from cycle 2 was concentrated. A reactor was charged with the concentrate from cycle 2, N-acetyliminodiacetic acid monohydrate (19.0 g), phosphorous acid (8.2 g) and 98% sulfuric acid (3 g). The mixture was heated to 110° C. and 42.2% formaldehyde (4.9 mL) was added drop wise over a one hour period. After another 1¾ hour at 110° C. the mixture was cooled to 25° C. The mixture was filtered and the solid was washed with water to give 14.7 g of N-(phosphonomethyl)iminodiacetic acid.

D) Cycle 4: The filtrate and wash from cycle 3 was concentrated. A reactor was charged with the concentrate from cycle 3, N-acetyliminodiacetic acid monohydrate (19.0 g), phosphorous acid (8.2 g), water (3 g) and 98% sulfuric acid (3 g). The mixture was heated to 110° C. and 42.2% formaldehyde (4.9 mL) was added drop wise over a one hour period. After another 1¾ hour at 110° C. the mixture was cooled to 25° C. The mixture was filtered and the solid was washed with water to give 17.2 g of N-(phosphonomethyl)iminodiacetic acid.

Example 11

This example illustrates the preparation of N-(phosphonomethyl)iminodiacetic acid from N-acetyliminodiacetic acid with recycle of the filtrate using methanesulfonic acid catalyst.

A) Cycle 1: A pressure reactor was charged with N-acetyliminodiacetic acid monohydrate (19.3 g), water (16.6 g), phosphorous acid (9.8 g) and methanesulfonic acid (15 g). The mixture was heated to 120° C. and 42% formaldehyde (6.9 mL) was added drop wise over a ¾ hour period. After another ¾ hour at 120° C. the mixture was cooled. The mixture was filtered and the solid was washed with water to give 17.6 g of N-(phosphonomethyl)iminodiacetic acid.

B) Cycle 2: The filtrate and wash from cycle 1 was concentrated. A reactor was charged with the concentrate from cycle 1, N-acetyliminodiacetic acid monohydrate (19.3 g), phosphorous acid (8.2 g), methane sulfonic acid (1.2 g) and water (10 mL). The mixture was heated to 120° C. and 42% formaldehyde (6.9 mL) was added drop wise over a ¾ hour period. After another ¾ hour at 120° C. the mixture was cooled. The mixture was filtered and the solid was washed with water to give 20.4 g of N-(phosphonomethyl)iminodiacetic acid.

C) Cycles 3 through 7: The filtrate and wash from the previous cycle was concentrated. A reactor was charged with the concentrate, N-acetyliminodiacetic acid monohydrate (19.3 g), phosphorous acid (8.2 g) and water (10 mL). The mixture was heated to 120° C. and 47% formaldehyde (5.8 mL) was added drop wise over a ¾ hour period. After another ¾ hour at 120° C. the mixture was cooled. The mixture was filtered and the solid was washed with water to give N-(phosphonomethyl) iminodiacetic acid.

Table 5 contains the results from similar runs for cycles 3–7.

TABLE 5

| Cycle | grams of (XV) |
|---|---|
| 3 | 18.9 |
| 4 | 21.2 |
| 5 | 20 |
| 6 | 18.9 |
| 7 | 18.0 |

Example 12

This example illustrates the preparation of N-(phosphonomethyl)iminodiacetic acid from N-acetyliminodiacetic acid using toluenesulfonic acid catalyst.

A pressure reactor was charged with N-acetyliminodiacetic acid monohydrate (19.3 g), water (16.6 g), phosphorous acid (9.8 g) and toluenesulfonic acid monohydrate (35.2 g). The mixture was heated to 120° C. and 47% formaldehyde (5.8 mL) was added drop wise over a ¾ hour period. After another ¾ hour at 120° C. the mixture was cooled. The mixture was filtered and the solid was washed with water to give 16.5 g of N-(phosphonomethyl)iminodiacetic acid.

Example 13

This example illustrates the that the addition of acetic acid to the amidocarboxymethylation reaction results in an increase in reaction rates compared to runs where no extra acetic acid was added.

The same apparatus described in Example 1 was used for these experiments. For Run A the amide feed solution had the following composition: 13.58 wt % acetamide, 5.11 wt % acetic acid, 81.3 wt % THF. For Run B the amide feed solution had the following composition: 6.08 wt % acetamide, 0.20 wt % acetic acid, 93.7 wt % THF. In both Run A and B the catalyst feed was 18.71 wt % $Co_2(CO)_8$ in THF. The feed ratios are noted below for each run.

| Components | Flow Rate mL/ min into stage 1 |
|---|---|
| Run A: | |
| Acetamide/THF/Acetic Acid Mixture | 24.18 |
| 48% Formalin(1000 ppm phosphate internal standard) | 6.19 |
| $Co_2(CO)_8$/THF | 4.63 |
| $CO:H_2$ (95:5) | 10.0 (L/min) |
| Run B: | |
| Acetamide/THF | 25.29 |
| 44.4% Formalin(1000 ppm phosphate internal standard) | 6.48 |
| $Co_2(CO)_8$/THF | 3.23 |
| $CO:H_2$ (95:5) | 10.0 (L/min) |

TABLE 6

| Run # | Elapsed Time (h:min) | Stage | Temp (° C.) | Stir Rate rpm | Yields mMole NAIDA | NAG | ACETAMIDE |
|---|---|---|---|---|---|---|---|
| A | 1:50 | 1 | 99 | 2000 | 36.6 | 10.8 | 3.1 |
|   | 1:56 | 2 | 99 | 2000 | 42.3 | 6.6 | 0.4 |
|   | 2:01 | 3 | 99 | 1000 | 43.5 | 4.5 | 0.06 |
| B | 1:58 | 1 | 98 | 2000 | 16.5 | 4.8 | 1.4 |
|   | 2:04 | 2 | 100 | 2000 | 22.6 | 1.8 | 0.0 |
|   | 2:10 | 3 | 100 | 1000 | 24.1 | 0.3 | 0.0 |

TABLE 6A

Rate(mole $L^{-1}$ $min^{-1}$) of Acetamide Disappearance in Stage 1

| Run A | 110 |
|---|---|
| Run B | 35 |

Example 14

This example illustrate using an extraction method to separate carbonylation catalyst from amidocarboxymethylation product stream.

In a 2-L autoclave, a mixture of acetamide (66.35 g, 1.12 mol), paraformaldehyde (76.33 g, 2.54 mol), dicobalt octacarbonyl (ca. 95%, 12.55 g, 0.035 mol), water (73 g, 4 mol), acetic acid (20 g, 0.33 mol), and tetrahydrofuran (480 mL) was vigorously agitated and heated to about 110° C. while maintaining a pressure of 3200 psi with a 95:5 $CO/H_2$ mixture. After about 1 hr, the mixture was cooled to 70° C. and toluene (750 mL) was added to the pressurized vessel. The complete mixture was then vigorously agitated for 30 min while cooling to 30° C. under 3200 psi of the $CO/H_2$ mixture. Agitation was terminated and the layers were allowed to separate for 30 min. The bottom layer, consisting of 317 g of an orange mixture, was discharged from the reactor and the upper phase, consisting of 1340 g of a dark brown solution was then recovered. Analysis of the two phases revealed that the lower phase contained 37% of the total cobalt recovered and was 50 wt % N-acetyliminodiacetic acid. Upon standing, the lower layer yielded crystals containing N-acetyliminodiacetic acid. The upper phase consisting mainly of the toluene and tetrahydrofuran solvents was found to contain 63% of the total cobalt recovered and was 1.3 wt % N-acetyliminodiacetic acid.

Example 15

This example demonstrates the adsorption of cobalt catalyst from carboxymethylation product streams using a cation exchange resin in a stirred batch reactor.

In these runs, a 300 mL autoclave equipped with an overhead vortex stirrer was loaded with acetamide (11.83 g, 0.200 mol), paraformaldehyde (13.60 g, 0.453 mol), water (12.89 g, 0.72 mol), acetic acid (4.21 g, 0.070 mol), $Co_2(CO)_8$ (4.048 g, 0.0118 mol), and 90 mL THF. The autoclave was pressurized to 3324 psi 95/5 $CO/H_2$ and heated at 110° C. for 35 minutes. The product stream of this reaction, containing 9520 ppm cobalt, was then transferred through a dip tube and into a second 300 mL autoclave, initially at ambient temperature, containing 31.62 g Amberlite 200 sulfonic acid resin ($H^+$ form). The autoclave was vented down to atmospheric pressure and sealed. The oxidation and adsorption were carried out at 110° C. for 3 hours. A sample was removed from the autoclave and the color of the decobalted solution was light yellow and contained 42 ppm cobalt, which is 0.37% of the amount initially charged.

Example 16

This example demonstrates the desorption of active cobalt catalyst from a cation exchange resin containing adsorbed $Co^{+2}$. The resin used was an Amberlite 200 resin which had been washed with a solution of cobalt acetate tetrahydrate to give a resin with a cobalt content of 4.7 wt %. To desorb cobalt and regenerate the active catalyst, a 2L autoclave equipped with an overhead vortex stirrer was loaded with acetamide (40.00 g, 0.677 mol), acetic acid (250 mL, 4.37 mol), 750 mL THF, and 107.10 g of the $Co^{+2}$ containing Amberlite 200 resin. The clave was heated to 130° C. under 3200 psi 70/30 $CO/H_2$. After 6 hours of reaction, the solution contained 4100 ppm cobalt, indicating that 77.9% of the cobalt had been desorbed from the resin. In-situ infrared spectroscopy of the desorption solution showed a peak at 1888 $cm^{-1}$ indicating the presence of cobalt tetracarbonyl anion, $Co(CO)_4^-$, which is also observed in solution during amidocarboxymethylation.

Example 17

This example illustrates the lower solubility of N-(phosphonomethyl)iminodiacetic acid in the phosphonomethylation reaction mixtures with higher acetic acid concentrations.

A typical phophonomthylation reactoin were run under similar conditions while varying the amount of acetic acid. Those runs with higher acetic acid concentrations were found to have lower GI concentrations in the filtrate:

|  | % Acetic Acid | % N-(Phosphonomethyl) iminodiacetic acid in solution |
|---|---|---|
| Run A | 10 | 3.3 |
| Run B | 20 | 2.6 |

Example 18

In a 2-L autoclave, a mixture of acetamide (66.35 g, 1.12 mol), paraformaldehyde (76.33 g, 2.54 mol), dicobalt octacarbonyl (ca. 95%, 12.55 g, 0.035 mol), water (73 g, 4 mol), acetic acid (20 g, 0.33 mol), and tetrahydrofuran (480 mL) was vigorously agitated and heated to about 110° C. while maintaining a pressure of 3200 psi with a 95:5 $CO/H_2$ mixture. After about 1 hr, the mixture was cooled to 70° C. and toluene (750 mL) was added to the pressurized vessel. The complete mixture was then vigorously agitated for 30 min while cooling to 30° C. under 3200 psi of the $CO/H_2$ mixture. Agitation was terminated and the layers were allowed to separate for 30 min. The bottom layer, consisting of 317 g of an orange mixture, was discharged from the reactor and the upper phase, consisting of 1340 g of a dark brown solution was then recovered. Analysis of the two phases revealed that the lower phase contained 37% of the total cobalt recovered and was 50 wt % N-acetyliminodiacetic acid. Upon standing, the lower layer yielded crystals containing N-acetyliminodiacetic acid. The upper phase consisting mainly of the toluene and tetrahydrofuran solvents was found to contain 63% of the total cobalt recovered and was 1.3 wt % N-acetyliminodiacetic acid.

Figure 2:
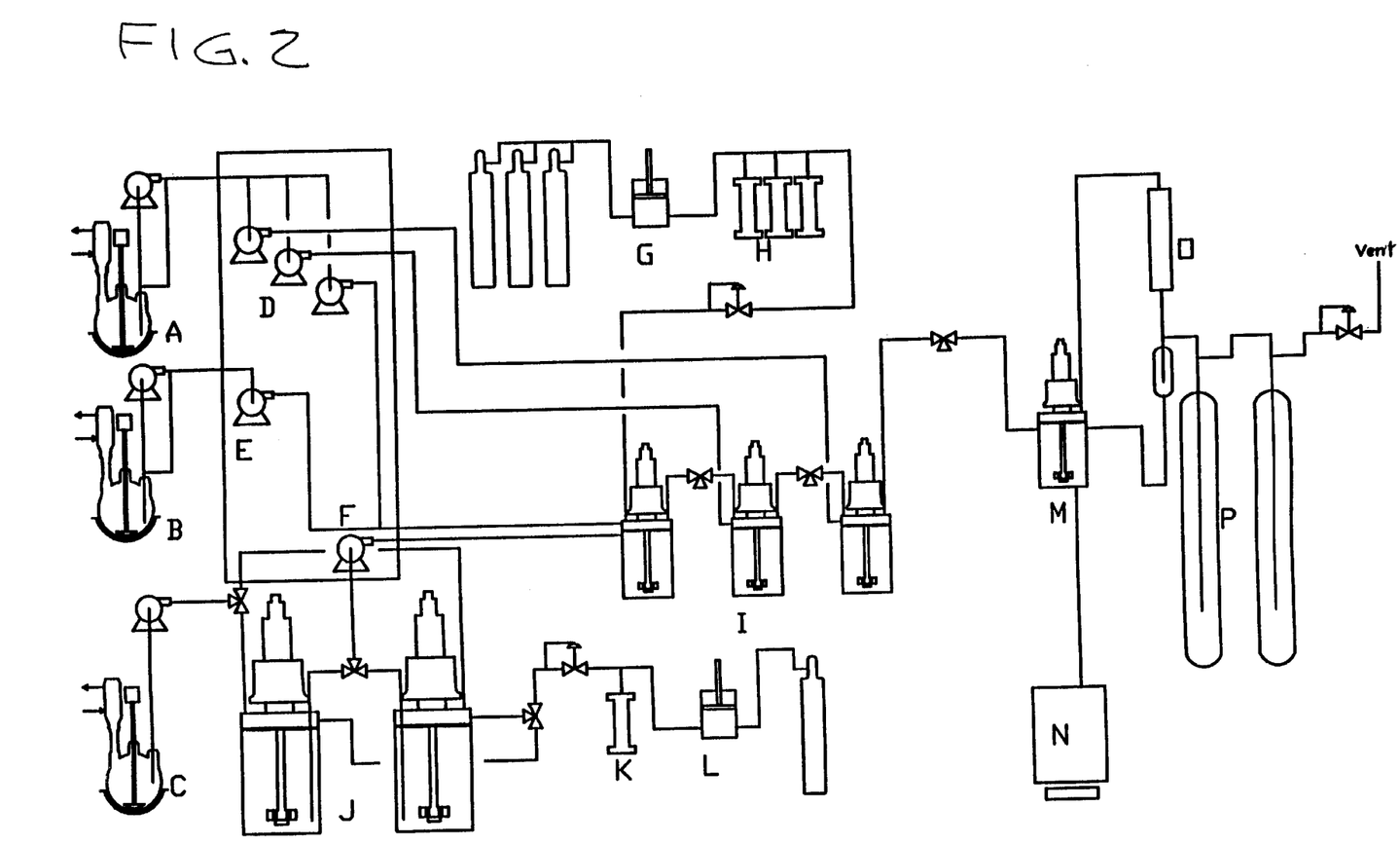
FIG. 2 is a schematic illustration of the continuous reactor system employed in Example 1.

FIG. 2 Captions
A Formalin Feed Vessel
B Amide Feed Vessel
C Catalyst Precursor Feed Vessel
D High Pressure Metering Pumps
E High Pressure Metering Pump
F High Pressure Metering Pump
G Synthesis Gas Compressor for Reaction System
H High pressure Synthesis Gas Reservoirs for Reaction System
I 1 L Autoclave Reaction System
J J 1 Gallon Autoclave Catalyst Regeneration System
K Synthesis Gas (70:30, $CO:H_2$)Reservoir for Catalyst Regeneration System
L Synthesis Gas Compressor for Catalyst Regeneration System
M High Pressure Liquid Gas Separator
N Product Tank
O Condenser
P Caustic Gas Scrubbers

What is claimed is:

1. A continuous process for the preparation of N-(phosphonomethyl)iminodiacetic acid, the process comprising
    (a) forming N-(acetyl)iminodiacetic acid in a amidocarboxymethylation reactor system into which is continuously fed a source of each of (1) acetamide or an acetamide derivative, (2) formaldehyde or a formaldehyde generator or derivative, (3) a carbonylation catalyst, (4) carbon monoxide, and optionally (5) hydrogen,
    (b) withdrawing from the amidocarboxymethylation reactor system an amidocarboxymethylation reaction product stream which contains N-(acetyl)iminodiacetic acid and the carbonylation catalyst,
    (c) separating the carbonylation catalyst from the amidocarboxymethylation reaction product stream to recover the carbonylation catalyst and form a catalyst depleted product stream which contains N-(acetyl)iminodiacetic acid,
    (d) returning the separated carbonylation catalyst to the amidocarboxymethylation reactor system,
    (e) optionally deacylating and cyclizing the N-(acetyl) iminodiacetic acid in the catalyst depleted product stream to form a 2,5-diketopiperazine,
    (f) reacting N-(acetyl)iminodiacetic acid or 2,5-diketopiperazine in the catalyst depleted product stream with a source of phosphorous and a source of formaldehyde in the presence of an acid to form a phosphonomethylation reaction product stream containing N-(phosphonomethyl)iminodiacetic acid and acetic acid,
    (g) precipitating N-(phosphonomethyl)iminodiacetic acid from the phosphonomethylation reaction product stream in the presence of acetic acid and recovering the precipitate to form a filtrate stream, (h) separating the filtrate stream into an acetic acid enriched stream and an acetic acid depleted stream, (i) feeding at least a portion of the acetic acid enriched stream to an acetamide synthesis reactor into which ammonia is simultaneously being fed to form an acetamide product stream, and (j) directly or indirectly feeding the acetamide product stream to the amidocarboxymethylation reactor system.

2. The process of claim 1 wherein the carbonylation catalyst in the amidocarboxymethylation reaction product stream comprises cobalt and is precipitated as an oxalate.

3. The process of claim 2 wherein the oxalate is calcined to form cobalt oxide and the cobalt oxide is regenerated before being returned to the amidocarboxymethylation reactor system.

4. The process of claim 1 wherein acetic acid is fed to the amidocarboxymethylation reactor system.

5. The process of claim 4 wherein a base pair having the formula $BH^+[Co(CO)_4]^-$ is fed to the amidocarboxymethylation reactor system and B is a protonated acetamide or protonated acetamide derivative.

6. The process of claim 4 wherein N-(acetyl) iminodiacetic acid or 2,5-diketopiperazine in the catalyst depleted product stream is reacted with a source of phosphorous and a source of formaldehyde in the presence of a sulfonic acid to form a phosphonomethylation reaction product stream containing N-(phosphonomethyl) iminodiacetic acid and acetic acid.

7. The process of claim 4 wherein acetic acid is fed to the reactor in which either step (f) or step (g) of claim 1 is being carried out such that the precipitation of step (g) occurs in the presence of added acetic acid.

8. The process of claim 4 wherein acetamide formed in step i of claim 1 is combined outside the amidocarboxymethylation reactor system with carbonylation catalyst which is separated from the amidocarboxymethylation reaction product stream in step (c) of claim 1.

9. The process of claim 1 wherein a base pair having the formula $BH^+[Co(CO)_4]^-$ is fed to the amidocarboxymethylation reactor system and B is a protonated acetamide or protonated acetamide derivative.

10. The process of claim 1 wherein the carbonylation catalyst is recovered by adsorption onto a bed of a support material having a species bound thereto that reversibly binds carbonylation catalyst present in the amidocarboxymethylation reaction product stream.

11. The process of claim 10 wherein the support material is a cation or anion exchange resin.

12. The process of claim 10 wherein the support material comprises an inorganic oxide.

13. The process of claim 10 wherein the support material comprises a cross-linked polymer.

14. The process of claim 10 wherein a phosphine species is on the surface of the support material.

15. The process of claim 10 wherein a species is on the surface of the support material and the species is selected from the group consisting of sulfonate, carboxylate, phosphate, alkylsulfonic acid, arylsulfonic acid, carboxylic acid, iminodiacetic acid, phosphonic acid, thiol, polyamine, alkylamine, arylamine, amide, pyridine, quaternary ammonium, quaternary alkylamine, quaternary alkylalkanolamine, and quaternary alkylbenzylamine species.

16. The process of claim 10 wherein the carbonylation catalyst is oxidized while adsorbed to the support material.

17. The process of claim 10 wherein the carbonylation catalyst is desorbed from the support material without being oxidized while adsorbed to the support material.

18. The process of claim 10 wherein the carbonylation catalyst is desorbed from the support material in the presence of acetamide.

19. The process of claim 10 wherein the carbonylation catalyst is regenerated while adsorbed to the solid support.

* * * * *